(12) United States Patent
Liu

(10) Patent No.: US 8,367,816 B2
(45) Date of Patent: Feb. 5, 2013

(54) COMPOSITIONS AND METHODS FOR THE TREATMENT OF SEPSIS AND OTHER DISORDERS INVOLVING PHOSPHOLIPASE $A_2$ INDUCTION

(76) Inventor: Maw-Shung Liu, Chesterfield, MO (US)

( * ) Notice: Subject to any disclaimer, the term of this patent is extended or adjusted under 35 U.S.C. 154(b) by 0 days.

(21) Appl. No.: 13/265,842

(22) PCT Filed: Mar. 25, 2010

(86) PCT No.: PCT/US2010/028622
§ 371 (c)(1),
(2), (4) Date: Oct. 21, 2011

(87) PCT Pub. No.: WO2010/123648
PCT Pub. Date: Oct. 28, 2010

(65) Prior Publication Data
US 2012/0041054 A1 Feb. 16, 2012

Related U.S. Application Data

(60) Provisional application No. 61/172,564, filed on Apr. 24, 2009.

(51) Int. Cl.
*C07H 21/04* (2006.01)
*A61K 48/00* (2006.01)
(52) U.S. Cl. ..................... 536/24.5; 536/23.1; 536/24.3; 536/24.31; 536/24.33; 514/44
(58) Field of Classification Search .................. None
See application file for complete search history.

(56) References Cited

U.S. PATENT DOCUMENTS

2005/0143331 A1* 6/2005 Bennett et al. .................. 514/44

* cited by examiner

Primary Examiner — Amy Bowman
(74) Attorney, Agent, or Firm — Martin L. McGregor

(57) ABSTRACT

The present invention provides antisense oligomers to $PLA_2$ to inhibit $PLA_2$ protein expression and enzyme activity, and to treat diseases and disorders associated with induced expression of $PLA_2$. In particular, the invention provides for the simultaneous inhibition of $cPLA_2$ and $sPLA_2$.

17 Claims, 8 Drawing Sheets

Fig. 1. Antisense ODN candidates designed specifically against human unspliced sPLA2 IIa DNA sequence, M22431.1.

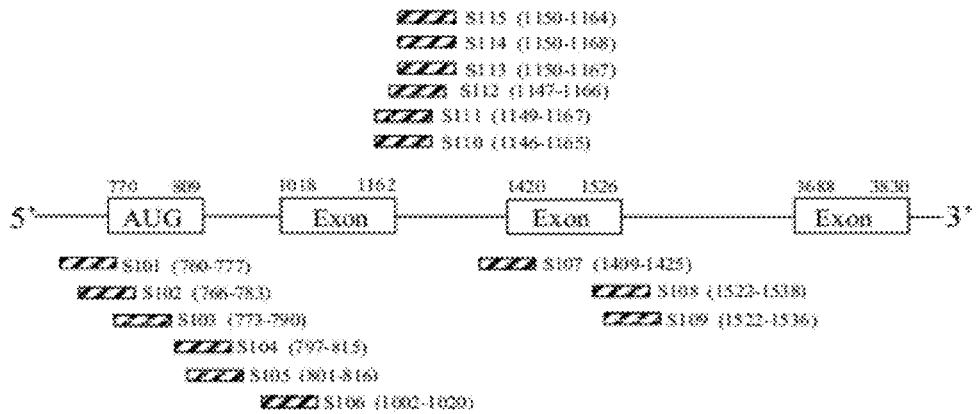

M22431.1: 3830 bp DNA, human RASF-A PLA2 gene encoding synovial phospholipase, exons 2 through 5 (Seilhamer, J.J., direct submission, 07-FEB-1989).

Numbers in the parenthesis indicate base positions.

Fig. 2. Antisense ODN candidates designed specifically against human spliced sPLA2 IIa mRNA sequence, NM_000300.3.

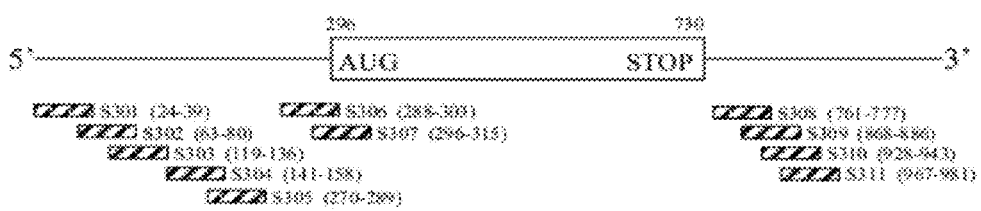

NM_000300.3: 1017 bp mRNA, Homo sapiens phospholipase A2, group IIA (platelets, synovial fluid) (PLA2G2A), transcript variant 1, mRNA. (Seilhamer et al., 1989; Guey et al., 2010).

Numbers in the parenthesis indicate base positions.

Fig. 3. Antisense ODN candidates designed specifically against human unspliced cPLA2 IVa DNA sequence, AY552098.1.

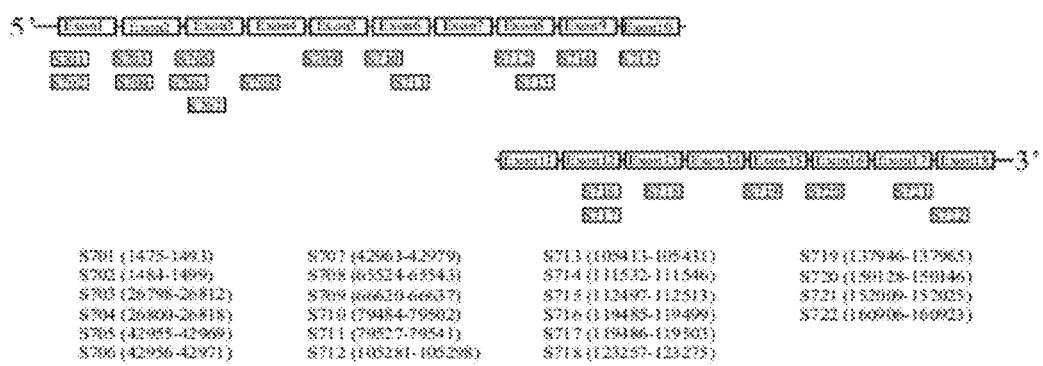

AY552098.1: 163504 bp DNA, Homo sapiens phospholipase A2, group IVA (cytosolic, calcium-dependent) (PLA2G4A) gene, complete cds. (Livingston et al., direct submission, 19-Feb-2004).

Numbers in the parenthesis indicate base positions.

Fig. 4. Antisense ODN candidates designed specifically against human spliced cPLA2 IVa mRNA sequence, NM_024420.2.

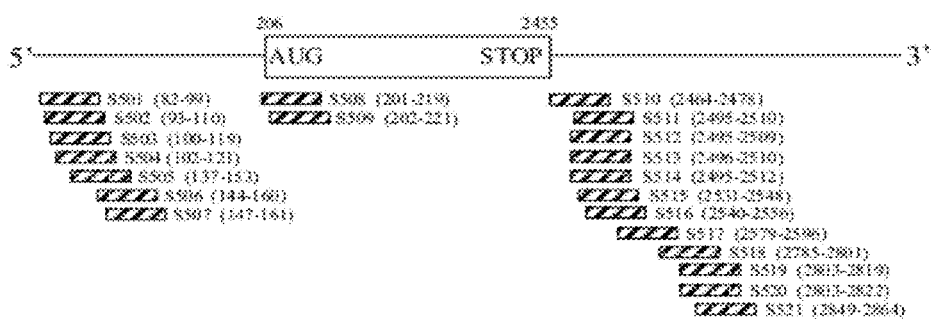

NM_024420.2: 2940 bp mRNA, Homo sapiens phospholipase A2, group IVA (cytosolic, calcium-dependent) (PLA2G4A), mRNA. (Clark et al., 1991; Su et al., 2010).

Numbers in the parenthesis indicate base positions.

Fig. 5. Antisense ODN candidates designed specifically against human/rat overlap sPLA₂ IIa mRNA sequences, NM_000300.3 (human) and M25148.1 (rat).

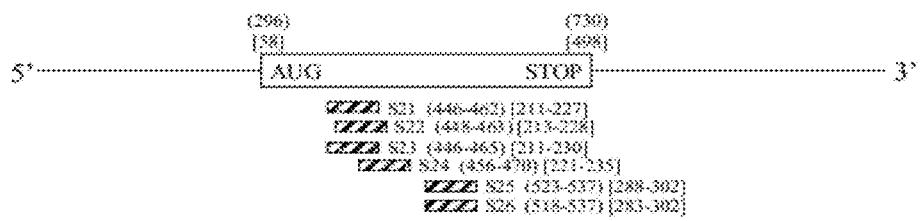

NM_000300.3: 1017 bp mRNA, Homo sapiens phospholipase A2, group IIA (platelets, synovial fluid) (PLA2G2A), transcript variant 1, mRNA. (Seilhamer et al., 1989; Guey et al., 2010).

M25148.1: 758 bp mRNA, Rat phospholipase A2 gene, complete cds. (Ishizaki et al., 1989).

( ) indicates base positions for human sequence, NM_000300.3. [ ] indicates base positions for rat sequence, M25148.1.

Fig. 6. Antisense ODN candidates designed specifically against human/rat overlap cPLA₂ IVa mRNA sequences, NM_024420.2 (human) and BC070940.1 (rat).

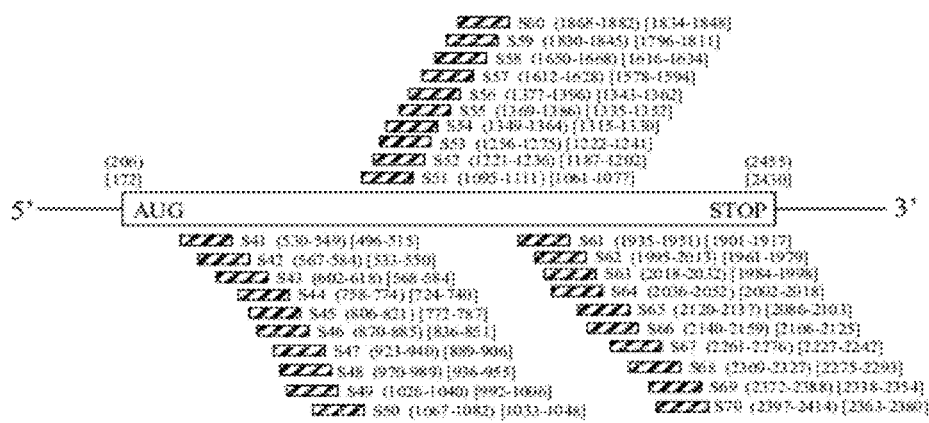

NM_024420.2: 2940 bp mRNA, Homo sapiens phospholipase A2, group IVA (cytosolic, calcium-dependent) (PLA2G4A), mRNA. (Clark et al., 1991; Su et al., 2010).

BC070940.1: 2853 bp mRNA, Rattus norvegicus phospholipase A2, group IVA (cytosolic, calcium-dependent), mRNA (cDNA clone MGC:91503 IMAGE:7098813), complete cds. (Strausberg et al., 2002).

( ) indicates base positions for human sequence, NM_024420.2. [ ] indicates base positions for rat sequence, BC070940.1.

Fig. 7. Analysis of vesicle size distribution of polycation/liposome complex, DOTAP/DOPE/PEI (25kD), prepared in this laboratory.

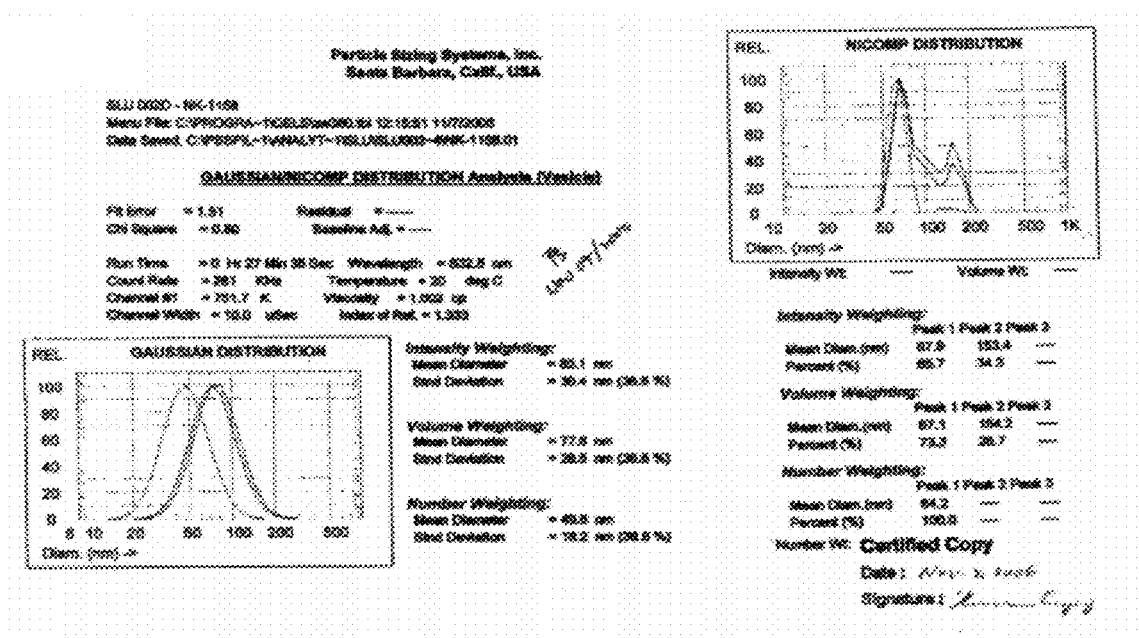

Fig. 8. Transfection efficiencies and cytotoxicities of various liposome and polycation/liposome preparations in human hepatoma Huh7 cell line.

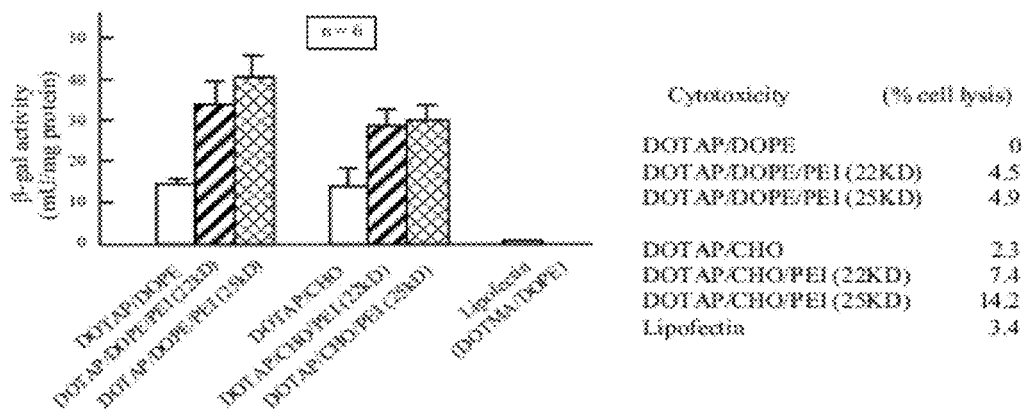

DOTAP: 1,2-dioleoyl-3-(trimethylammonio)propane.
DOPE: dioleyl-L-α-phosphatidylethanolamine.
DOTAM: N-[1-(2,3-dioleoyl)propyl]-N-N-trimethol ammonium chloride.
CHO: cholesterol.
PEI: polyethyleneimine.

Fig. 9. Effects of SEQ ID NO: 1 (S101) and SEQ ID NO: 2 (S104) on the inhibition of human sPLA2 IIa protein expression in human hepatoma HepG2 cell line.
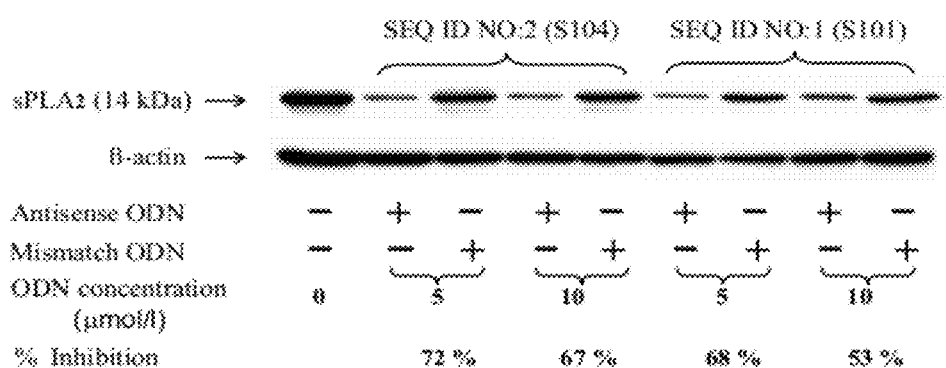
Fig. 10. Effects of SEQ ID NO: 9 (S707) on the inhibition of human cPLA2 IVa protein expression in human monocytic leukemia U937 cell line.
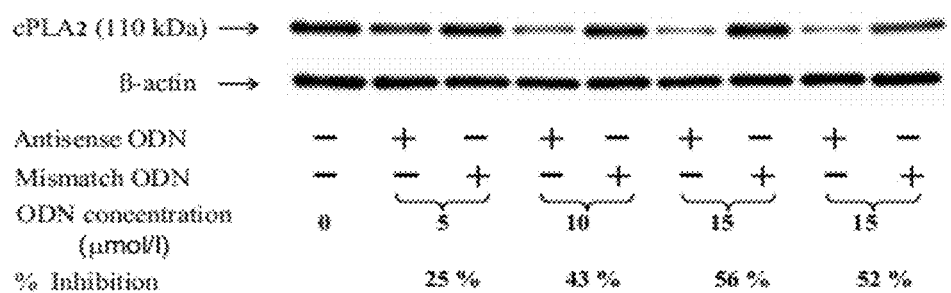

Fig. 11. Effects of SEQ ID NO:13 (S23) on the inhibition of human sPLA2 IIa protein expression in human hepatoma HepG2 cell line.
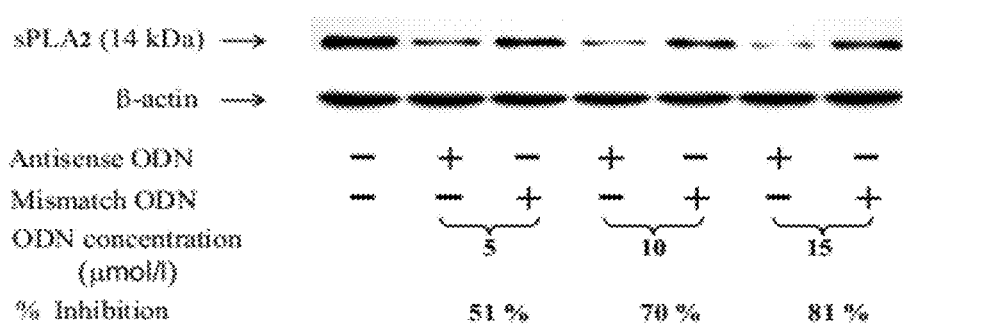
Fig. 12. Effects of SEQ NO: 18 (S56) on the inhibition of human cPLA2 IVa protein expression in human monocytic leukemia U937 cell line.
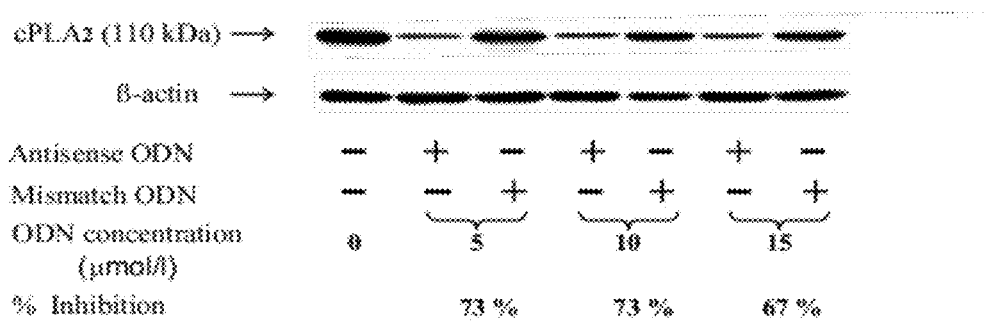

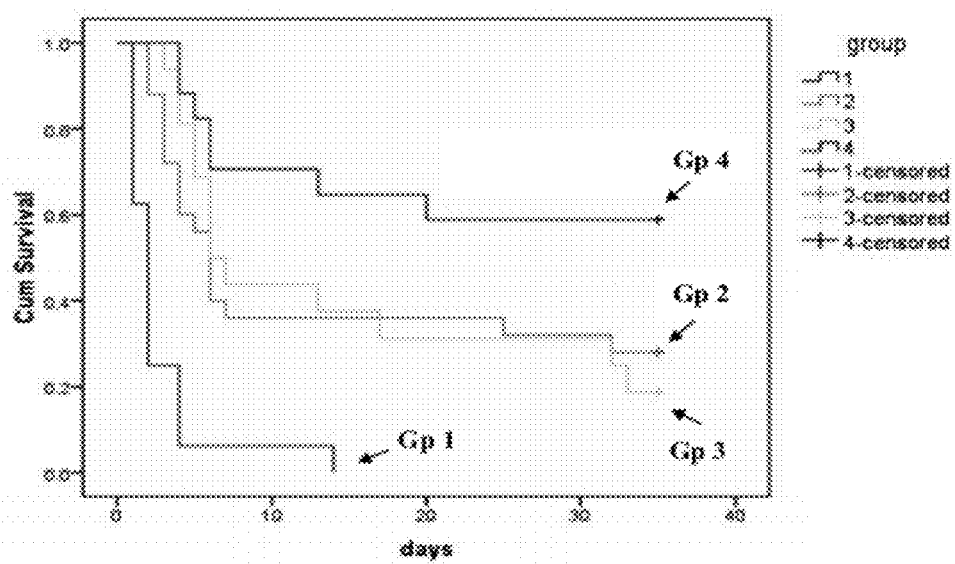

Fig. 13. Effects of antisense molecules, SEQ ID NO:13 and SEQ ID NO:18, on the rate of survival of septic animals treated concurrently with or without antibiotics.

+ (censored) indicates animals that survived and terminated at day 35 (efficacy endpoint).

| Group | N | Experimental conditions | Median survival time (day) | 35-day Survival rate (%) |
|---|---|---|---|---|
| 1 | 16 | CLP | 2.0 | 0 |
| 2 | 25 | CLP + AB | 6.0 | 28.0 |
| 3 | 16 | CLP + AB + MM-ODN | 6.5 | 18.8 |
| 4 | 17 | CLP + AB + AS-ODN | 35.0 | 58.8 |

CLP: cecal ligation and puncture
AB: antibiotic
MM-ODN: mismatch oligonucleotide
AS-ODN: antisense oligonucleotide Survival curves were analyzed by Cox proportional-hazards regression model
  Gp 1 vs Gp 2:  $p < 0.05$
  Gp 4 vs Gp 2:  $p < 0.05$
  Gp 4 vs Gp 3:  $p < 0.05$
  Gp 3 vs Gp 2:  $p > 0.05$

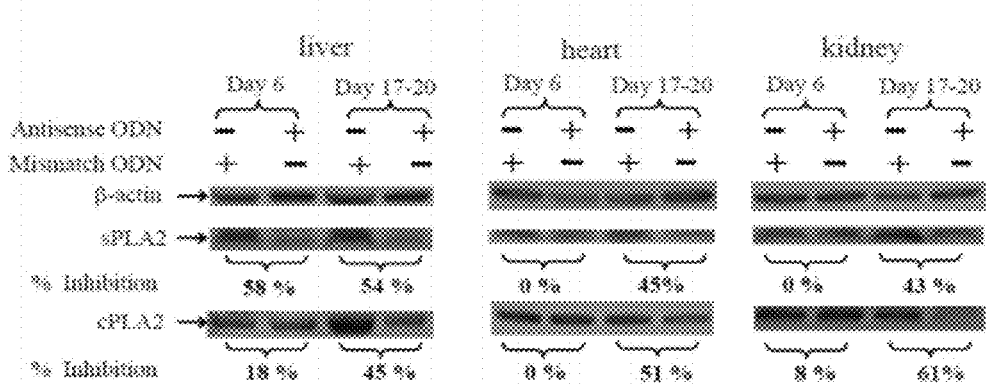
Fig. 14. Effects of antisense molecules, SEQ ID NO:13 and SEQ ID NO:18, on the inhibition of sPLA$_2$ IIa and cPLA$_2$ IVa protein expression in various organs harvested from postmortem septic rats.

SEQUENCE LISTING

```
<160> NUMBER OF SEQ ID NOS: 23

<210> SEQ ID NO 1
<211> LENGTH: 18
<212> TYPE: DNA
<213> ORGANISM: Artificial Sequence
<220> FEATURE:
<223> OTHER INFORMATION: Synthetic primer

<400> SEQUENCE: 1
gtcttcatgg taagagtt                                                        18

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
tcttaccaaa gatcatgat                                                       19

<210> SEQ ID NO 3
<211> LENGTH: 15
<212> TYPE: DNA
<213> ORGANISM: Artificial Sequence
<220> FEATURE:
<223> OTHER INFORMATION: Synthetic primer

<400> SEQUENCE: 3
ggactcttac cacag                                                           15

<210> SEQ ID NO 4
<211> LENGTH: 18
<212> TYPE: DNA
<213> ORGANISM: Artificial Sequence
<220> FEATURE:
<223> OTHER INFORMATION: Synthetic primer

<400> SEQUENCE: 4
ctcaccgatc cgttgcat                                                        18

<210> SEQ ID NO 5
<211> LENGTH: 19
<212> TYPE: DNA
<213> ORGANISM: Artificial Sequence
<220> FEATURE:
<223> OTHER INFORMATION: Synthetic primer
```

```
<400> SEQUENCE: 5
cctcaccgat ccgttgcat                                              19

<210> SEQ ID NO 6
<211> LENGTH: 15
<212> TYPE: DNA
<213> ORGANISM: Artificial Sequence
<220> FEATURE:
<223> OTHER INFORMATION: Synthetic primer

<400> SEQUENCE: 6
tttattcaga agaga                                                  15

<210> SEQ ID NO 7
<211> LENGTH: 15
<212> TYPE: DNA
<213> ORGANISM: Artificial Sequence
<220> FEATURE:
<223> OTHER INFORMATION: Synthetic primer

<400> SEQUENCE: 7
gctccacctg gaaat                                                  15

<210> SEQ ID NO 8
<211> LENGTH: 16
<212> TYPE: DNA
<213> ORGANISM: Artificial Sequence
<220> FEATURE:
<223> OTHER INFORMATION: Synthetic primer

<400> SEQUENCE: 8
gtgctccacc tggaaa                                                 16

<210> SEQ ID NO 9
<211> LENGTH: 17
<212> TYPE: DNA
<213> ORGANISM: Artificial Sequence
<220> FEATURE:
<223> OTHER INFORMATION: Synthetic primer

<400> SEQUENCE: 9
gaatactggt gctccac                                                17

<210> SEQ ID NO 10
<211> LENGTH: 18
<212> TYPE: DNA
<213> ORGANISM: Artificial Sequence
<220> FEATURE:
<223> OTHER INFORMATION: Synthetic primer

<400> SEQUENCE: 10
tttatcacct gcaaatag                                               18

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
cctcaatgcc tctagctttc                                             20
```

```
<210> SEQ ID NO 12
<211> LENGTH: 19
<212> TYPE: DNA
<213> ORGANISM: Artificial Sequence
<220> FEATURE:
<223> OTHER INFORMATION: Synthetic primer

<400> SEQUENCE: 12
tctataaatg acattttgg                                                19

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ttgggggatc ctctgccacc                                               20

<210> SEQ ID NO 14
<211> LENGTH: 15
<212> TYPE: DNA
<213> ORGANISM: Artificial Sequence
<220> FEATURE:
<223> OTHER INFORMATION: Synthetic primer

<400> SEQUENCE: 14
catccttggg ggatc                                                    15

<210> SEQ ID NO 15
<211> LENGTH: 15
<212> TYPE: DNA
<213> ORGANISM: Artificial Sequence
<220> FEATURE:
<223> OTHER INFORMATION: Synthetic primer

<400> SEQUENCE: 15
gtgccacatc cacgt                                                    15

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
gtgccacatc cacgtttctc                                               20

<210> SEQ ID NO 17
<211> LENGTH: 16
<212> TYPE: DNA
<213> ORGANISM: Artificial Sequence
<220> FEATURE:
<223> OTHER INFORMATION: Synthetic primer

<400> SEQUENCE: 17
agaatcccac catggc                                                   16

<210> SEQ ID NO 18
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 18
aaaggcactg ccccagacac                                               20

<210> SEQ ID NO 19
<211> LENGTH: 19
<212> TYPE: DNA
<213> ORGANISM: Artificial Sequence
<220> FEATURE:
<223> OTHER INFORMATION: Synthetic primer

<400> SEQUENCE: 19
ttcccagcac gtccttctc                                                19

<210> SEQ ID NO 20
<211> LENGTH: 15
<212> TYPE: DNA
<213> ORGANISM: Artificial Sequence
<220> FEATURE:
<223> OTHER INFORMATION: Synthetic primer

<400> SEQUENCE: 20
gggatacggc aggtt                                                    15

<210> SEQ ID NO 21
<211> LENGTH: 15
<212> TYPE: DNA
<213> ORGANISM: Artificial Sequence
<220> FEATURE:
<223> OTHER INFORMATION: Synthetic primer

<400> SEQUENCE: 21
aggatcaatc tttgg                                                    15

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
ttggtggatc ctctggcacc                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
aaagtcactg ccccacacac                                               20
```

COMPOSITIONS AND METHODS FOR THE TREATMENT OF SEPSIS AND OTHER DISORDERS INVOLVING PHOSPHOLIPASE $A_2$ INDUCTION

The present application claims benefit of priority to U.S. Ser. No. 61/172,564, filed Apr. 24, 2009, the entire contents of which are hereby incorporated by reference and further claims benefit of priority to International PCT Application Serial No. PCT/US2010/028622 the entire contents of which are hereby incorporated by reference, this is a national phase application under 35 USC 371.

BACKGROUND OF THE INVENTION

1. Field of the Invention

The present invention relates generally to the fields of cell biology, molecular biology and medicine. More particularly, it concerns use of antisense oligomers to $PLA_2$ (phospholipase $A_2$) to inhibit $PLA_2$ protein expression and enzyme activity, and to treat diseases and disorders associated with induced expression of $PLA_2$, especially $cPLA_2$ (cytosolic $PLA_2$), and $sPLA_2$ (secretory $PLA_2$).

2. Description of Related Art

Sepsis is a prevalent disease which leads to death or disability by multiple organ failure. Although many pharmacological agents and therapeutic interventions have been developed for the treatment of sepsis and septic shock, the problems of organ dysfunction involving liver, heart, lung, kidney and circulating blood cells, etc., continue to affect millions of people throughout the world (Angus et al., 2001; Parrillo, 1991; Centers for Disease Control, 1990; Chaby, 1999). Most of the pharmacological agents that have been developed to control sepsis and septic shock have met with limited success because they are aimed at specific organ or cell type. Since sepsis elicited $PLA_2$ overexpression in many organs and tissues, and the overexpressed $PLA_2$ is closely linked to multiple organ failure (Vadas and Pruzanski, 1983; Liu, 1990; Endo et al., 1995; Nagase et al., 2000), a logical approach for treatment of sepsis is to prevent the overexpression of $PLA_2$ genes.

Antisense inhibition has been developed for the treatment of diseases resulting from overexpression of genes (Jansen and Zangemeister-Wittke, 2002; Phillips, 2001; Jaaskelainen and Urtti, 2002; Riijcken et al., 2002; Griesenbach et al., 2002; Merdan et al., 2002). An antisense oligonucleotide (ODN) is a single-stranded synthetic DNA with a specific sequence to hybridize a specific mRNA. The hybridization leads to a reduction in the protein level. The specificity and uniqueness of the antisense ODN toward single gene and its efficient cellular uptake and wild distribution among many organs (Phillips et al., 2000; Phillips, 2001; Jaaskelainen and Urtti, 2002; Mohuczy and Phillips, 2002), make antisense ODN strategy a most desirable approach for treatment of sepsis, because sepsis-induced $PLA_2$ overexpression takes place in multiple organs. Other advantages include that antisense ODN can be used as a drug and it has an action that lasts for either days for short-term or weeks for long-term treatments. In addition, antisense ODN is safe and it fails to induce toxic effects such as inflammation and immune responses (Phillips et al., 2000; Phillips, 2001; Jaaskelainen and Urtti, 2002; Mohuczy and Phillips, 2002). Additional benefit of employing antisense ODN strategy to correct sepsis-elicited $PLA_2$ overexpression resides on its ability to "knock-down" rather than "knock-out" the overexpressed gene so that it reduces overactive protein yet permits normal physiology (Phillips, 2001).

Many potential therapies that inhibit $PLA_2$ activities, the subsequent enzymatic pathways, and mediators, have been investigated in clinical trials (Abraham et al., 2003; Bernard et al., 1997; Opal et al., 2004) and animal studies (Nagase et al., 2003). Inhibition of $sPLA_2$ activity with a selective enzyme inhibitor in patients with sepsis and organ failure had no overall survival benefit (28-day all-cause mortality), but had a significant treatment effect when drug was given earlier, i.e., within 18 hrs from the onset of the first sepsis-induced organ failure (Abraham et al., 2003) Inhibition of cyclooxygenase pathway with ibuprofen in sepsis patients reduced physiological abnormalities but did not improve the rate of survival at 30 days (Bernard et al., 1997). Treatment of sepsis patients with a recombinant human platelet-activating factor (PAF) acetylhydrolase did not decrease 28-day all-cause mortality (Opal et al., 2004) Inhibition of $cPLA_2$ activity by a potent enzymatic inhibitor attenuated acute lung injury induced by lipopolysaccharide in mice (Nagase et al., 2003). The efficacy of the afore-mentioned agents clinically has been less overwhelming. Thus, improved methods for treating sepsis continue to be highly desired.

SUMMARY OF THE INVENTION

Thus, in accordance with the present invention, there is provided an antisense oligonucleotide comprising the sequence of SEQ ID NO:1 (5'-GTCTTCATGGTAAGAGTT-3'), SEQ ID NO:2 (5'-TCTTACCAAAGATCATGAT-3'), SEQ ID NO:3 (5'-GGACTCTTACCACAG-3'), SEQ ID NO:4 (5'-CTCACCGATCCGTTGCAT-3'), SEQ ID NO:5 (5'-CCTCACCGATCCGTTGCAT-3'), SEQ ID NO:6 (5'-TT-TATTCAGAAGAGA-3'), SEQ ID NO:7 (5'-GCTCCAC-CTGGAAAT-3'), SEQ ID NO:8 (5'-GTGCTCCACCTG-GAAA-3'), SEQ ID NO:9 (5'-GAATACTGGTGCTCCAC-3'), SEQ ID NO:10 (5'-TTTATCACCTGCAAATAG-3'), SEQ ID NO:11 (5'-CCTCAATGCCTCTAGCTTTC-3'), SEQ ID NO:12 (5'-TCTATAAATGACATTTTGG-3'), SEQ ID NO:13 (5'-TTGGGGGATCCTCTGCCACC-3'), SEQ ID NO:14 (5'-CATCCTTGGGGGATC-3'), SEQ ID NO:15 (5'-GTGCCACATCCACGT-3'), SEQ ID NO:17 (5'-AGAATC-CCACCATGGC-3'), SEQ ID NO:18 (5'-AAAGGCACTGC-CCCAGACAC-3'), SEQ ID NO:19 (5'-TTCCCAGCACGTCCTTCTC-3'), SEQ ID NO:20 (5'-GGGATACGGCAGGTT-3') or SEQ ID NO:21 (5'-AGGATCAATCTTTGG-3').

The antisense oligonucleotide may be dispersed in a pharmaceutical buffer, diluent or excipient. It may also be formulated in a lipid carrier. The oligonucleotide may further comprise a nuclear targeting sequence, and/or may comprise one or more modified or non-natural nucleotides. The antisense oligonucleotide may be 15-50 bases, 15-40 bases, 15-30 bases, 15-25 bases, or 15-20 bases. The antisense oligonucleotide may consist of SEQ ID NOS:1-21. An especially preferred embodiment provides an antisense oligonucleotide of 18 to 25 bases comprising a sequence selected from the group consisting of -, SEQ ID NO:13 (5'-TTGGGGGATCCTCT-GCCACC-3'), or SEQ ID NO:18 (5'-AAAGGCACTGC-CCCAGACAC-3') and the selected oligonucleotide when administered to a predictive animal model that mimics a disease pathogenesis process in humans causes a reduction of the protein product encoded by the target gene by at least 20% in a major organ selected from the group comprising liver, kidney, or heart.

In another embodiment, there is provided a method of reducing phospholipase $A_2$ expression in a cell comprising contacting said cell with one or more antisense oligonucleotides comprising a sequence selected from the group consisting of SEQ ID NO:1 (5'-GTCTTCATGGTAAGAGTT-3'), SEQ ID NO:2 (5'-TCTTACCAAAGATCATGAT-3'), SEQ ID NO:3 (5'-GGACTCTTACCACAG-3'), SEQ ID NO:4 (5'-CTCACCGATCCGTTGCAT-3'), SEQ ID NO:5 (5'-CCTCACCGATCCGTTGCAT-3'), SEQ ID NO:6 (5'-TTTATTCAGAAGAGA-3'), SEQ ID NO:7 (5'-GCTCCAC-CTGGAAAT-3'), SEQ ID NO:8 (5'-GTGCTCCACCTG-GAAA-3'), SEQ ID NO:9 (5'-GAATACTGGTGCTCCAC-3'), SEQ ID NO:10 (5'-TTTATCACCTGCAAATAG-3'), SEQ ID NO:11 (5'-CCTCAATGCCTCTAGCTTTC-3'), SEQ ID NO:12 (5'-TCTATAAATGACATTTTGG-3'), SEQ ID NO:13 (5'-TTGGGGGATCCTCTGCCACC-3'), SEQ ID NO:14 (5'-CATCCTTGGGGGATC-3'), SEQ ID NO:15 (5'-GTGCCACATCCACGT-3'), SEQ ID NO:17 (5'-AGAATC-CCACCATGGC-3'). SEQ ID NO:18 (5'-AAAGGCACTGC-CCCAGACAC-3'), SEQ ID NO:19 (5'-TTCCCAGCACGTCCTTCTC-3'), SEQ ID NO:20 (5'-GGGATACGGCAGGTT-3') or SEQ ID NO:21 (5'-AGGATCAATCTTTGG-3').

The subject may suffer from sepsis, septic shock, inflammation, inflammatory bowel disease; trauma, rheumatoid arthritis, adult respiratory distress syndrome (ARDS), asthma, rhinitis, diabetes type II, psoriasis, ischemic disease, atherosclerosis, restenosis, platelet aggregation, ulceration or cancer. The method may comprise the use of at least two different oligonucleotides, at least one selected from (i) SEQ ID NOS:1-6 and SEQ ID NOS:13-15, and (ii) at least one selected from SEQ ID NOS:7-12 and SEQ ID NOS:17-21. The cell may be a human cell or a rodent cell, and may be located in a living subject. The antisense oligonucleotide may be dispersed in a pharmaceutical buffer, diluent or excipient for in vivo uses. It may also be formulated in a lipid carrier. The oligonucleotide may further comprise a nuclear targeting sequence, and/or may comprise one or more modified or non-natural nucleotides. The antisense oligonucleotide may be 15-50 bases, 15-40 bases, 15-30 bases, 15-25 bases, or 15-20 bases. The antisense oligonucleotide may consists of SEQ ID NOS:1-21. An especially preferred method provides two antisense oligonucleotide consisting of antisense oligonucleotides of 18 to 25 bases: one comprising SEQ ID NO:13 (5'-TTGGGGGATCCTCTGCCACC-3') and the other comprising SEQ ID NO:18 (5'-AAAGGCACTGCCCCAGA-CAC-3'), and when administered to a predictive animal model that mimics a disease pathogenesis process in humans the selected antisense oligonucleotides cause a reduction of both protein products encoded by the genes targeted by said oligonucleotides by at least 20% in a major organ selected from the group comprising liver, kidney, or heart.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects. As used herein "antisense oligonucleotide" means a nucleotide sequence that binds to a target molecule and reduces production of an expression product of the target molecule. "Target molecule" means a gene, RNA strand, mRNA or other component of an expression process within a cell to which an antisense nucleotide binds and reduces expression of a product directly or indirectly.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1—Antisense ODN candidates designed specifically against human unspliced sPLA$_2$ IIa DNA sequence, M22431.1.

FIG. 2—Antisense ODN candidates designed specifically against human spliced sPLA$_2$ IIa mRNA sequence, NM_000300.3.

FIG. 3—Antisense ODN candidates designed specifically against human unspliced cPLA$_2$ IVa DNA sequence, AY552098.1.

FIG. 4—Antisense ODN candidates designed specifically against human spliced cPLA$_2$ IVa mRNA sequence, NM_024420.2

FIG. 5—Antisense ODN candidates designed specifically against human/rat overlap sPLA$_2$ IIa mRNA sequences, NM_000300 (human) and M25148.1 (rat).

FIG. 6—Antisense ODN candidates designed specifically against human/rat overlap cPLA$_2$ IVa mRNA sequences, NM_024420.2 (human) and BC070940.1 (rat).

FIG. 7—Analysis of vesicle size distribution of polycation/liposome complex, DOTAP/DOPE/PEI (25 kD), prepared in this laboratory.

FIG. 8—Transfection efficiencies and cytotoxicities of various liposome and polycation/liposome preparations in human hepatoma Huh7 cell line.

FIG. 9—Effects of SEQ ID NO: 1 (S101) and SEQ ID NO:2 (S104) on the inhibition of human sPLA2 IIa protein expression in human hepatoma HepG2 cell line.

FIG. 10—Effects of SEQ ID NO:9 (S707) on the inhibition of human cPLA$_2$ IVa protein expression in human monocytic leukemia U937 cell line.

FIG. 11—Effects of SEQ ID NO:13 (S23) on the inhibition of human sPLA$_2$ IVa protein expression in human hepatoma HepG2 cell line.

FIG. 12—Effects of SEQ ID NO:18 (S56) on the inhibition of human cPLA$_2$ IVa protein expression in human monocytic leukemia U937 cell line.

FIG. 13—Effects of antisense molecules, SEQ ID NO:13 and SEQ ID NO:18, on the survival of septic animals treated concurrently with or without antibiotics.

FIG. 14—Effects of antisense molecules, SEQ ID NO:13 and SEQ ID NO:18, on the inhibition of sPLA$_2$ IIa and cPLA$_2$ IVa protein expression in various organs harvested from postmortem septic rats.

DESCRIPTION OF ILLUSTRATIVE EMBODIMENTS

As discussed above, sepsis is a prevalent disease which leads to death or disability by multiple organ failure, and continues to affect millions of people throughout the world. Most of the therapeutic agents that have been developed to control sepsis have met with limited success because they are aimed at specific organ or cell type. In addition, many potential therapies based on pharmacological agents that inhibit PLA$_2$ activities, the subsequent enzymatic pathways, or the mediators, have been investigated in clinical trials and animal studies. Though they have improved certain symptoms and organ functions but not the eventual outcome, i.e., the mortality.

The inventor surmised that the explanation for the less than overwhelming efficacy of existing therapies is that the pharmacological agents are directed to either a single PLA$_2$ isoenzyme, a single subsequent pathway, or a single mediator. There are at least 19 isoenzymes that possess PLA$_2$ activities, have been identified in mammals (van den Bosch, 1985). Since the two major forms of PLA$_2$ isoenzymes, namely the sPLA$_2$ and cPLA$_2$, are both overexpressed during sepsis (Abraham et al., 2003; Bernard et al., 1997; Opal et al., 2004; Vadas et al., 1988), the inventor believes that a simultaneous correction of the overexpression of both genes has a higher probability of improving the eventual outcome. In this application, it is shown that a highly efficient intracellular delivery system capable of carrying multiple antisense molecules can target both sPLA$_2$ and cPLA$_2$ genes. Furthermore, the use of two different antisense oligonucleotides (one against sPLA$_2$ and the other against cPLA$_2$) with concurrent antibiotic treatment, is capable of increasing the 35-day survival rate of septic animals from 28.0% to 58.8% ($p<0.05$). The antisense treatment also reduces their target protein expression by 18-61% in major organs such as liver, heart, and kidney in septic animals. The use of this antisense gene strategy can thus succeed in improving the eventual outcome where other pharmacological therapies have failed.

I. PHOSPHOLIPASE A$_2$

Phospholipases A$_2$ (PLA$_2$) are upstream regulators of many inflammatory processes. This particular phospholipase specifically recognizes the sn-2 acyl bond of phospholipids and catalytically hydrolyzes the bond releasing arachidonic acid and lysophospholipids. Upon downstream modification by cyclooxygenases, arachidonic acid is modified into active compounds called eicosanoids. Eicosanoids include prostaglandins and leukotrienes which are categorized as inflammatory mediators.

PLA$_2$ are commonly found in mammalian tissues as well as insect and snake venom. Venom from both snakes and insects is largely composed of melittin which is a stimulant of PLA$_2$. Due to the increased presence and activity of PLA$_2$ resulting from a snake or insect bite, arachidonic acid is released from the phospholipid membrane disproportionately. As a result, inflammation and pain occur at the site. There are also prokaryotic A$_2$ phospholipases.

There are at least 19 isoenzymes possessing PLA$_2$ activities that have been identified in mammals (van den Bosch, 1985). Based on their distinct characteristics in tissue origin, molecular mass, Ca$^{2+}$ requirement, substrate specificity, and regulatory function, PLA$_2$ isoenzymes are classified into three major groups: 1) sPLA$_2$, a Ca$^{2+}$-dependent (mM range) and low molecular weight (13-15 kDa) form; 2) cPLA$_2$, a Ca$^{2+}$-dependent (μM range) and high molecular weight (85-110 kDa) form; and 3) iPLA$_2$, a Ca$^{2+}$-independent and plasmalogan substrate-specific form (mol wt 40-85 kDa). Functionally, sPLA$_2$ and cPLA$_2$ regulate a number of biological processes including initiation of AA metabolism, production of eicosanoids and PAF, and generation of lysophospholipid-derived mediators (van den Bosch, 1985). The phospholipases A$_2$ include several unrelated protein families with common enzymatic activity. Two most notable families are secretory and cytosolic phospholipases A$_2$. Other families include Ca$^{2+}$ independent PLA$_2$ (iPLA$_2$) and lipoprotein-associated PLA$_2$s (1p-PLA$_2$), also known as platelet activating factor acetylhydrolase (PAF-AH).

A. Secretory Phospholipase A$_2$ (sPLA$_2$)

The extracellular forms of phospholipases A$_2$ have been isolated from different venoms (snake, bee, and wasp), from virtually every studied mammalian tissue (including pancreas and kidney) as well as from bacteria. They require Ca$^{2+}$ for activity. Pancreatic PLA$_2$ serve for the initial digestion of phospholipid compounds in dietary fat. Venom phospholipases help to immobilize prey by promoting cell lysis.

B. Cytosolic Phospholipases A$_2$ (cPLA$_2$)

The intracellular PLA$_2$ are also Ca$^{2+}$-dependent, but they have completely different 3D structure and significantly larger than secretary PLA$_2$ (more than 700 residues). They include C2 domain and large catalytic domain. These phospholipases are involved in cell signaling processes, such as inflammatory response. The produced arachadonic acid is both a signaling molecule and the precursor for other signaling molecules termed eicosanoids. These include leukotrienes and prostaglandins. Some eicosanoids are synthesized from diacylglycerol, released from the lipid bilayer by phospholipase C.

II. ANTISENSE TECHNOLOGY

A. Antisense Oligonucleotides

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

Steric blocking antisense (RNase-H independent antisense) interferes with gene expression or other mRNA-dependent cellular processes by binding to a target sequence of mRNA and getting in the way of other processes. Steric blocking antisense includes 2'-O alkyl (usually in chimeras with RNase-H dependent antisense), peptide nucleic acid (PNA), locked nucleic acid (LNA) and Morpholino antisense.

In general, antisense oligonucleotides will be in the range of 10-50 nucleotides in length, with the balance being struck between the needed length for specificity, and cost and complexity of greater lengths. In general, the antisense oligonucleotides will be in ranges of 10-40, 10-30, 10-25, 10-20, 15-30, 15-25, 18-25, or 18-23 nucleotides in length.

In addition, fragments, variants and analogs of the antisense oligonucleotides may be utilized. A "fragment" of a molecule, such as any of the oligonucleotide sequences of the present invention, is meant to refer to any nucleotide subset of the molecule. A "variant" of such molecule is meant to refer a naturally occurring molecule substantially similar to either the entire molecule or a fragment thereof. An "analog" of a molecule can be without limitation a paralogous or orthologous molecule, e.g., a homologous molecule from the same species or from different species, respectively, i.e., an antisense oligonucleotide complementary to the equivalent region of the gene in a different species, which therefore may have slight changes in the sequence.

Further, the antisense oligonucleotides of the invention can be labeled or conjugated to a reporter molecule, such that the antisense oligonucleotide of the invention may be traced and/or detected in the organism. Any label or reporter molecule that allow its detection may be suitable, e.g., biotin, fluorescein, rhodamine, 4-(4'-Dimethylamino-phenylazo)benzoic acid ("Dabcyl"); 4-(4'-Dimethylamino-phenylazo)sulfonic acid (sulfonyl chloride) ("Dabsyl"); 5-((2-aminoethyl)-amino)-naphtalene-1-sulfonic acid ("EDANS"); psoralene derivatives, haptens, cyanines, acridines, fluorescent rhodol derivatives, cholesterol derivatives, radioactive labels, as well as metal particles (e.g., gold).

B. Modifications

As mentioned, the antisense oligonucleotides of the invention can be chemically modified, so as to possess improved endonuclease resistance. Any chemical modification which confers resistance towards endonucleases, such as, but not limited to phosphorothioation or 2-O-methylation, may be adopted. A variety of well-known, alternative oligonucleotide chemistries may be used (see, e.g., U.S. Patent Publications 2007/0213292, 2008/0032945, 2007/0287831, etc.), particularly single-stranded complementary oligonucleotides comprising 2' methoxyethyl, 2'-fluoro, and morpholino bases (see e.g., Summerton and Weller, 1997). The oligonucleotide may include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). Also contemplated are locked nucleic acid (LNA) and peptide nucleic acids (PNA).

Peptide nucleic acids (PNAs) are nonionic DNA mimics that have outstanding potential for recognizing duplex DNA (Kaihatsu et al., 2004; Nielsen et al., 1991). PNAs can be readily synthesized and bind to complementary sequences by standard Watson-Crick base-pairing (Egholm et al., 1993), allowing them to target any sequence within the genome without the need for complex synthetic protocols or design considerations. Strand invasion of duplex DNA by PNAs is not hindered by phosphate-phosphate repulsion and is both rapid and stable (Kaihatsu et al., 2004; Nielsen et al., 1991). Applications for strand invasion by PNAs include creation of artificial primosomes (Demidov et al., 2001), inhibition of transcription (Larsen and Nielsen, 1996), activation of transcription (Mollegaard et al., 1994), and directed mutagenesis (Faruqi et al., 1998). PNAs would provide a general and potent strategy for probing the structure and function of chromosomal DNA in living systems if their remarkable strand invasion abilities could be efficiently applied inside cells.

Strand invasion by PNAs in cell-free systems is most potent at sequences that are partially single-stranded (Bentin and Nielsen, 1996; Zhang et al., 2000). Assembly of RNA polymerase and transcription factors into the pre-initiation complex on DNA induces the formation of a structure known as the open complex that contains several bases of single-stranded DNA (Holstege et al., 1997; Kahl et al., 2000). The exceptional ability of PNAs to recognize duplex DNA allows them to intercept the open complex of an actively transcribed gene without a requirement for preincubation. The open complex is formed during transcription of all genes and PNAs can be synthesized to target any transcription initiation site. Therefore, antigene PNAs that target an open complex at a promoter region within chromosomal DNA would have the potential to be general tools for controlling transcription initiation inside cells.

A locked nucleic acid (LNA), often referred to as inaccessible RNA, is a modified RNA nucleotide (Elmen et al., 2008). The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. Such oligomers are commercially available. The locked ribose conformation enhances base stacking and backbone pre-organization. This significantly increases the thermal stability (melting temperature) of oligonucleotides (Kaur et al., 2006). LNA bases may be included in a DNA backbone, by they can also be in a backbone of LNA, 2'-O-methyl RNA, 2'-methoxyethyl RNA, or 2'-fluoro RNA. These molecules may utilize either a phosphodiester or phosphorothioate backbone.

Other oligonucleotide modifications can be made to produce oligonucleotides. For example, stability against nuclease degradation has been achieved by introducing a phosphorothioate (P=S) backbone linkage at the 3' end for exonuclease resistance and 2' modifications (2'-OMe, 2'-F and related) for endonuclease resistance (WO 2005115481; Li et al., 2005; Choung et al., 2006). A motif having entirely of 2'-O-methyl and 2'-fluoro nucleotides has shown enhanced plasma stability and increased in vitro potency (Allerson et al., 2005). The incorporation of 2'-O-Me and 2'-O-MOE does not have a notable effect on activity (Prakash et al., 2005).

Sequences containing a 4'-thioribose modification have been shown to have a stability 600 times greater than that of natural RNA (Hoshika et al, 2004). Crystal structure studies reveal that 4'-thioriboses adopt conformations very similar to the C3'-endo pucker observed for unmodified sugars in the native duplex (Haeberli et al., 2005). Stretches of 4'-thio-RNA were well tolerated in both the guide and nonguide strands. However, optimization of both the number and the placement of 4'-thioribonucleosides is necessary for maximal potency.

In the boranophosphate linkage, a non-bridging phosphodiester oxygen is replaced by an isoelectronic borane (BH3-) moiety. Boranophosphate siRNAs have been synthesized by enzymatic routes using T7 RNA polymerase and a boranophosphate ribonucleoside triphosphate in the transcription reaction. Boranophosphate siRNAs are more active than native siRNAs if the center of the guide strand is not modified, and they may be at least ten times more nuclease resistant than unmodified siRNAs (Hall et al., 2004; Hall et al., 2006).

Certain terminal conjugates have been reported to improve or direct cellular uptake. For example, NAAs conjugated with cholesterol improve in vitro and in vivo cell permeation in liver cells (Rand et al., 2005). Soutschek et al. (2004) have reported on the use of chemically-stabilized and cholesterol-conjugated siRNAs have markedly improved pharmacological properties in vitro and in vivo. Chemically-stabilized siRNAs with partial phosphorothioate backbone and 2'-O-methyl sugar modifications on the sense and antisense strands (discussed above) showed significantly enhanced resistance towards degradation by exo- and endonucleases in serum and in tissue homogenates, and the conjugation of cholesterol to the 3' end of the sense strand of an oligonucleotides by means of a pyrrolidine linker does not result in a significant loss of gene-silencing activity in cell culture. These study demonstrates that cholesterol conjugation significantly improves in vivo pharmacological properties of oligonucleotides.

U.S. Patent Publication 2008/0015162, incorporated herein by reference, provide additional examples of nucleic acid analogs useful in the present invention. The following excerpts are derived from that document and are exemplary in nature only.

In certain embodiments, oligomeric compounds comprise one or more modified monomers, including 2'-modified sugars, such as BNA's and monomers (e.g., nucleosides and nucleotides) with 2'-substituents such as allyl, amino, azido, thio, O-allyl, O—$C_1$-$C_{10}$ alkyl, —$OCF_3$, O—$(CH_2)_2$—O—$CH_3$, 2'-O$(CH_2)_2$S$CH_3$, O—$(CH_2)_2$—O—N($R_m$)($R_n$), or O—$CH_2$—C(=O)—N($R_m$)($R_n$), where each $R_m$ and $R_n$ is, independently, H or substituted or unsubstituted $C_1$-$C_{10}$ alkyl.

In certain embodiments, the oligomeric compounds including, but not limited to short oligomers of the present invention, comprise one or more high affinity monomers provided that the oligomeric compound does not comprise a nucleotide comprising a 2'-O$(CH_2)_n$H, wherein n is one to six. In certain embodiments, the oligomeric compounds including, but not limited to short oligomers of the present invention, comprise one or more high affinity monomer provided that the oligomeric compound does not comprise a nucleotide comprising a 2'-O$CH_3$ or a 2'-O$(CH_2)_2$O$CH_3$. In certain embodiments, the oligomeric compounds comprise one or more high affinity monomers provided that the oligomeric compound does not comprise a α-L-methyleneoxy (4'-$CH_2$—O-2') BNA and/or a β-D-methyleneoxy (4'-$CH_2$—O-2') BNA.

Certain BNA's have been prepared and disclosed in the patent literature as well as in scientific literature (Singh et al., 1998; Koshkin and Dunford, 1998; Wahlestedt et al., 2000; Kumar et al., 1998; WO 94/14226; WO 2005/021570; Singh et al, 1998; examples of issued US patents and published applications that disclose BNAs include, for example, U.S. Pat. Nos. 7,053,207; 6,268,490; 6,770,748; 6,794,499; 7,034,133; and 6,525,191; and U.S. Patent Publication Nos. 2004/0171570; 2004/0219565; 2004/0014959; 2003/0207841; 2004/0143114; and 2003/0082807.

Also provided herein are BNAs in which the 2'-hydroxyl group of the ribosyl sugar ring is linked to the 4' carbon atom of the sugar ring thereby forming a methyleneoxy (4'-$CH_2$—O-2') linkage to form the bicyclic sugar moiety (reviewed in Elayadi et al., 2001; see also U.S. Pat. Nos. 6,268,490 and 6,670,461). The linkage can be a methylene (—$CH_2$—) group bridging the 2' oxygen atom and the 4' carbon atom, for which the term methyleneoxy (4'-$CH_2$—O-2') BNA is used for the bicyclic moiety; in the case of an ethylene group in this position, the term ethyleneoxy (4'-$CH_2CH_2$—O-2') BNA is used (Singh et al., 1998; Morita et al., 2003). Methyleneoxy (4'-$CH_2$—O-2') BNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising BNAs have been described (Wahlestedt et al., 2000).

An isomer of methyleneoxy (4'-$CH_2$—O-2') BNA that has also been discussed is α-L-methyleneoxy (4'-$CH_2$—O-2') BNA which has been shown to have superior stability against a 3'-exonuclease. The α-L-methyleneoxy (4'-$CH_2$—O-2') BNA's were incorporated into antisense gapmers and chimeras that showed potent antisense activity (Frieden et al., 2003).

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin and Dunford, 1998). BNAs and preparation thereof are also described in WO 98/39352 and WO 99/14226.

Analogs of methyleneoxy (4'-$CH_2$—O-2') BNA, phosphorothioate-methyleneoxy (4'-$CH_2$—O-2') BNA and 2'-thio-BNAs, have also been prepared (Kumar et al., 1998). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., 1998). In addition, 2'-amino- and 2'-methylamino-BNA's have been prepared and the thermal stability of their duplexes with complementary RNA and DNA strands has been previously reported.

Modified sugar moieties are well known and can be used to alter, typically increase, the affinity of oligomers for targets and/or increase nuclease resistance. A representative list of modified sugars includes, but is not limited to, bicyclic modified sugars (BNA's), including methyleneoxy (4'-$CH_2$—O-2') BNA and ethyleneoxy (4'-$(CH_2)_2$—O-2' bridge) BNA; substituted sugars, especially 2'-substituted sugars having a 2'-F, 2'-O$CH_3$ or a 2'-O$(CH_2)_2$—O$CH_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909;

5,610,300; 5,627,053; 5,639,873; 5,646,265; 5,658,873; 5,670,633; 5,792,747; 5,700,920; 6,531,584; and 6,600,032; and WO 2005/121371.

C. Pharmaceutical Preparations

Pharmaceutical compositions of the present invention comprise an effective amount an antisense oligonucleotide dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains an antisense oligonucleotide or additional active ingredient will be known to those of skill in the art in light of the present disclosure, as exemplified by Remington's Pharmaceutical Sciences, 18$^{th}$ Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18$^{th}$ Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The compounds of the invention may comprise different types of carriers depending on whether it is to be administered in solid, liquid or aerosol form, and whether it need to be sterile for such routes of administration as injection.

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compounds of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In particular embodiments, antisense oligonucleotide compositions of the present invention are prepared for administration by such routes as oral ingestion. In these embodiments, the solid composition may comprise, for example, solutions, suspensions, emulsions, tablets, pills, capsules (e.g., hard or soft shelled gelatin capsules), delayed release capsules, sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain specific embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum. After insertion, suppositories soften, melt or dissolve in the cavity. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

Therapeutic effective amounts, or dosing, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$, found to be effective in in vitro as well as in vivo animal models. In general, dosage is from 0.01 µg to 10 mg per kg of body weight, and may be given once or more daily, weekly, monthly or yearly, or even once every 2 to 20 years. Persons of ordinary skill in the art can easily estimate repetition rates for dosing based on measured residence times and concentrations of the antisense oligonucleotide in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 10 mg per kg of body weight, once or more daily.

Optimal dosage used for treatment of the inflammatory conditions is 1-2 mg/kg/day given daily for between 5 up to 14 days, or given in one or two doses of 1-2 mg/kg/day after inflammation.

A particular formulation for delivery antisense oligonucleotides is a liposome. A liposome is a small vesicle, usually made of phospholipids. The lipids in the plasma membrane are chiefly phospholipids like phosphatidylethanolamine and phosphatidylcholine. Phospholipids are amphiphilic with the hydrocarbon tail of the molecule being hydrophobic; its polar head hydrophilic. Liposomes can be composed of naturally-derived phospholipids with mixed lipid chains (like egg phosphatidylethanolamine), or of pure surfactant components like DOPE (dioleoylphosphatidylethanolamine). Liposomes, usually but not by definition, contain a core of aqueous solution; lipid spheres that contain no aqueous material are called micelles, however, reverse micelles can be made to encompass an aqueous environment.

D. Routes of Administration

The compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by mucosally, inhalation, orthotopic, intradermal, subcutaneous, intramuscular, intraperitoneal or intravenous injection. Such compositions would normally be administered as pharmaceutically acceptable compositions, described supra. Other methods or any combination of the foregoing as would be known to one of ordinary skill in the art (see, for example, Remington's Pharmaceutical Sciences, $18^{th}$ Ed. Mack Printing Company, 1990, incorporated herein by reference).

E. Production of Oligonucleotides

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in European Patent 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959, 463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference.

Antisense oligonucleotides of the present invention may also be produced recombinantly, such as in a bacterium, yeast or insect cell. Various aspects of recombinant production, and materials used therefor, are set out in detail below.

1. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous" or "homologous." Similarly, an enhancer may be one naturally associated with a nucleic acid sequence, located either downstream or upstream of that sequence. Alternatively, certain advantages will be gained by positioning the coding nucleic acid segment under the control of a recombinant, exogenous or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in prokaryotic recombinant DNA construction include the β-lactamase (penicillinase), lactose and tryptophan (trp) promoter systems.

Naturally, it will be important to employ a promoter and/or enhancer that effectively directs the expression of the DNA segment in the organelle, cell, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, world-wide-web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

b. Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, incorporated by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Particular embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of 2-24 hr, the cells are collected by centrifugation and washed to remove residual media.

j. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Viruses may thus be utilized that encode and express p40 or p75. Non-limiting examples of virus vectors that may be used to deliver a p40 or p75 nucleic acid are described below.

Adenoviral Vectors. A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

AAV Vectors. The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) has a high frequency of integration and it can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviral Vectors. Retroviruses have the ability to integrate their genes into the host genome, transferring a large amount of foreign genetic material, infecting a broad spectrum of species and cell types and of being packaged in special cell-lines (Miller, 1992). In order to construct a retroviral vector, a nucleic acid (e.g., one encoding a protein of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubinstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and that is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other Viral Vectors. Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

Modified Viruses. A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Ex Vivo Transformation

Methods for transfecting vascular cells and tissues removed from an organism in an ex vivo setting are known to those of skill in the art. For example, cannine endothelial cells have been genetically altered by retroival gene tranfer in vitro and transplanted into a canine (Wilson et al., 1989). In another example, yucatan minipig endothelial cells were tranfected by retrovirus in vitro and transplated into an artery using a double-ballonw catheter (Nabel et al., 1989). Thus, it is contemplated that cells or tissues may be removed and tranfected ex vivo using the nucleic acids of the present invention. In particular aspects, the transplanted cells or tissues may be placed into an organism. In preferred facets, a nucleic acid is expressed in the transplanted cells or tissues.

b. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus oocytes* (Harland and Weintraub, 1985). The amount of vector used may vary upon the nature of the antigen as well as the organelle, cell, tissue or organism used.

c. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazzeri, 1995), sorghum (Battraw and Hall, 1991), maize (Bhattacharjee et al., 1997), wheat (He et al., 1994) and tomato (Tsukada et al., 1989).

d. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

e. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

f. Sonication Loading

Additional embodiments of the present invention include the introduction of a nucleic acid by direct sonic loading. LTK⁻ fibroblasts have been transfected with the thymidine kinase gene by sonication loading (Fechheimer et al., 1987).

g. Liposome-Mediated Transfection

In a further embodiment of the invention, a nucleic acid may be entrapped in a lipid complex such as, for example, a liposome. As discussed above, liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

h. Receptor-Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

i. Microprojectile Bombardment

Microprojectile bombardment techniques can be used to introduce a nucleic acid into at least one organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang and Russell, 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

An illustrative embodiment of a method for delivering DNA into a cell by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

3. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

In certain embodiments, the host cell or tissue may be comprised in at least one organism. In certain embodiments, the organism may be, but is not limited to, a prokayote (e.g., a eubacteria, an archaea) or a eukaryote (yeast), as would be understood by one of ordinary skill in the art (see, for example, webpage phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials (world-wide-web at atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5α, JM109, and KCB, bacilli such as *Bacillus subtilis*; and other enterobacteriaceae such as *Salmonella typhimurium, Serratia marcescens*, various *Pseudomonas* specie, as well as a number of commercially available bacterial hosts such as SURE® Competent Cells and SOLOPACK™ Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

4. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE'S COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REx™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed," i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g., 8 M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

III. TREATMENT OF INFLAMMATORY DISORDERS

The present inventor has identified a series of antisense oligonucleotides against both cytosolic phospholipase $A_2$ ($cPLA_2$) mRNA and secretory phospholipase $A_2$ ($sPLA_2$), mRNA that reduce the expression of their respective targets. Surprisingly, by using at least one antisense oligonucleotide against each of these targets greatly improves the clinical result.

In one embodiment, the pharmaceutical composition of the invention is intended for the treatment of inflammation processes related to $PLA_2$ overexpression, such as rheumatoid arthritis, ARDS, asthma, rhinitis, idiopathic pulmonary fibrosis, peritonitis, cardiovascular inflammation, myocardial ischemia, reperfusion injury, atherosclerosis, sepsis, trauma, diabetes type II, retinopathy, psoriasis, gastrointestinal inflammation, cirrhosis and inflammatory bowel disease, neurodegenerative diseases such as Alzheimer's disease, Parkinson's disease and amyotrophic lateral sclerosis, as well as brain ischemic and traumatic injury, i.e., in all diseases where oxidative stress has a significant role in its pathogenesis, and in which there is accelerated release of eicosanoids and superoxides by reactive microglia.

Of particular interest is the treatment of sepsis and septic shock. Sepsis is a medical condition characterized by a whole-body inflammatory state (called a systemic inflammatory response syndrome or SIRS) and the presence of a known or suspected infection. The body may develop this inflammatory response to microbes in the blood, urine, lungs, skin, or other tissues. An incorrect layman's term for sepsis is blood poisoning, more aptly applied to septicemia, referring to the presence of pathogenic organisms in the blood-stream, which can lead to sepsis.

Sepsis is usually treated in the intensive care unit with intravenous fluids and antibiotics. If fluid replacement is insufficient to maintain blood pressure, specific vasopressor drugs can be used. Artificial ventilation and dialysis may be needed to support the function of the lungs and kidneys, respectively. To guide therapy, a central venous catheter and an arterial catheter may be placed. Sepsis patients require preventive measures for deep vein thrombosis, stress ulcers and pressure ulcers, unless other conditions prevent this.

Severe sepsis occurs when sepsis leads to organ dysfunction, low blood pressure (hypotension), or insufficient blood flow (hypoperfusion) to one or more organs (causing, for example, lactic acidosis, decreased urine production, or altered mental status). Sepsis can lead to septic shock, multiple organ dysfunction syndrome (formerly known as multiple organ failure), and death. Organ dysfunction results from sepsis-induced hypotension (<90 mm Hg or a reduction of 40 mm Hg from baseline) and diffuse intravascular coagulation, among other things.

Bacteremia, the presence of viable bacteria in the bloodstream, when associated with certain dental procedures can cause bacterial infection of the heart valves (known as endocarditis) in high-risk patients. Conversely, a systemic inflammatory response syndrome can occur in patients without the presence of infection, for example in those with burns, polytrauma, or the initial state in pancreatitis and chemical pneumonitis.

In addition to symptoms related to the provoking infection, sepsis is characterized by evidence of acute inflammation present throughout the entire body, and is, therefore, frequently associated with fever and elevated white blood cell count (leukocytosis) or low white blood cell count and lower-than-average temperature. The modern concept of sepsis is that the host's immune response to the infection causes most of the symptoms of sepsis, resulting in hemodynamic consequences and damage to organs. This host response has been termed systemic inflammatory response syndrome (SIRS) and is characterized by hemodynamic compromise and resultant metabolic derangement. Outward physical symptoms of this response frequently include a high heart rate (above 90 beats per minute), high respiratory rate (above 20 breaths per minute), elevated WBC count (above 12,000) and elevated or decrease in body temperature (under 36° C. or over 38° C.). Sepsis is differentiated from SIRS by the presence of a known pathogen. For example SIRS and a positive blood culture for a pathogen indicates the presence of sepsis. Without a known infection you can not classify the above symptoms as sepsis, only SIRS.

This immunological response causes widespread activation of acute-phase proteins, affecting the complement system and the coagulation pathways, which then cause damage to the vasculature as well as to the organs. Various neuroendocrine counter-regulatory systems are then activated as well, often compounding the problem. Even with immediate and aggressive treatment, this may progress to multiple organ dysfunction syndrome and eventually death.

In the U.S., sepsis is the second-leading cause of death in non-coronary ICU patients, and the tenth-most-common cause of death overall according to data from the Centers for Disease Control and Prevention (the first being multiple organ failure). Sepsis is common and also more dangerous in elderly, immunocompromised, and critically-ill patients. It occurs in 1-2% of all hospitalizations and accounts for as much as 25% of intensive-care unit (ICU) bed utilization. It is a major cause of death in intensive-care units worldwide, with mortality rates that range from 20% for sepsis to 40% for severe sepsis to >60% for septic shock. These figures are also controversially linked to the (sometimes unnecessary) use of sedation in intubated and intensive-care patients, because of the high rates of sepsis and general infection that commonly develop more frequently in sedated patients. Also, the overuse of antibiotics has led to the development of super-strains, such as MRSA, which runs rampants in hospitals, and often makes the beds of intensive care patients become death beds, often as a result of septic wounds.

Sepsis is considered present if infection is highly suspected or proven and two or more of the following systemic inflammatory response syndrome (SIRS) criteria are met:

Heart rate >90 beats per minute (tachycardia)
Body temperature <36° C. (97° F.) or >38° C. (100° F.) (hypothermia or fever)
Respiratory rate >20 breaths per minute or, on blood gas, a $P_aCO_2$ less than 32 mm Hg (4.3 kPa) (tachypnea or hypocapnia due to hyperventilation)
White blood cell count <4,000 cells/mm$^3$ or >12,000 cells/mm$^3$ (<4×10$^9$ or >12×10$^9$ cells/L), or greater than 10% band forms (immature white blood cells) (leukopenia, leukocytosis, or bandemia).
Fever and leukocytosis are features of the acute-phase reaction, while tachycardia is often the initial sign of hemodynamic compromise. Tachypnea may be related to the increased metabolic stress due to infection and inflammation, but may also be an ominous sign of inadequate perfusion resulting in the onset of anaerobic cellular metabolism.

Note that SIRS criteria are very non-specific, and must be interpreted carefully within the clinical context. These criteria exist primarily for the purpose of more objectively classifying critically-ill patients so that future clinical studies may be more rigorous and more easily reproducible. Consensus definitions, however, continue to evolve, with the latest expanding the list of signs and symptoms of sepsis to reflect clinical bedside experience.

To qualify as sepsis, there must be an infection suspected or proven (by culture, stain, or polymerase chain reaction (PCR)), or a clinical syndrome pathognomonic for infection. Specific evidence for infection includes WBCs in normally sterile fluid (such as urine or cerebrospinal fluid (CSF), evidence of a perforated viscus (free air on abdominal x-ray or CT scan, signs of acute peritonitis), abnormal chest x-ray (CXR) consistent with pneumonia (with focal opacification), or petechiae, purpura, or purpura fulminans.

The more critical subsets of sepsis are severe sepsis (sepsis with acute organ dysfunction) and septic shock (sepsis with refractory arterial hypotension). As an alternative, when two or more of the systemic inflammatory response syndrome criteria are met without evidence of infection, patients may be diagnosed simply with "SIRS." Patients with SIRS and acute organ dysfunction may be termed "severe SIRS." Patients are defined as having "severe sepsis" if they have sepsis plus signs of systemic hypoperfusion: either end-organ dysfunction or serum lactate greater than 4 mmol/dL. Other signs include oliguria and altered mental status. Patients are defined as having septic shock if they have sepsis plus hypotension after aggressive fluid resuscitation (typically upwards of 6 liters or 40 ml/kg of crystalloid).

Examples of end-organ dysfunction include acute lung injury or acute respiratory distress syndrome, encephalopathy, or dysfunction affecting liver (disruption of protein synthetic function and metabolic functions), kidney (oliguria and anuria, electrolyte abnormalities, volume overload), and heart (systolic and diastolic heart failure).

IV. COMBINATION THERAPIES

An antisense oligonucleotide composition of the present invention may be administered in combination with another agent for the treatment of an inflammatory disorder involving induced $PLA_2$ expression and epithelial cell disorder involving pathologic apoptosis. By combining agents, an additive effect may be achieved while not increasing the toxicity (if any) associated with a monotherapy. In addition, it is possible that more than additive effect ("synergism") may be observed. Thus, combination therapies are a common way to exploit new therapeutic regimens.

The antisense oligonucleotide treatment may precede, be concurrent with and/or follow the other agent(s) by intervals ranging from minutes to weeks. In embodiments where the antisene oligonucleotide treatment and other agent(s) are applied separately to a cell, tissue or organism, one would generally ensure that a significant period of time did not expire between the time of each delivery, such that the antisene oligonucleotide treatment and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the antisene oligonucleotide treatment. In other aspects, one or more agents may be administered within of from substantially simultaneously, about 1 minute, about 5 minutes, about 10 minutes, about 20 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1 week, about 2 weeks, about 3 weeks, about 4 weeks, about 5 weeks, about 6 weeks, about 7 weeks or about 8 weeks or more, and any range derivable therein, prior to and/or after administering the p40-60 AA peptide.

Various combination regimens of the antisene oligonucleotide treatment and one or more agents may be employed. Non-limiting examples of such combinations are shown below, wherein an antisene oligonucleotide treatment is "A" and an agent is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Thus, antisense oligonucleotide therapies of the present invention can be used in conjunction with other therapies that are used for the treatment of disorders discussed above. In particular, anti-inflammatory agents such as steroids and NSAIDs may be employed, and in the case of sepsis, also antibiotics.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Design of Antisense Oligonucleotide Candidates

Homology comparison. The first step to design an optimal antisense oligodeoxynucleotide (ODN) molecule is to compare the homology of different sequences reported from different laboratories cloning the same protein (Phillips et al., 2000; Jansen and Zangemeister-Wittke, 2002; Phillips, 2001; Mohuczy and Phillips, 2002; Phillips and Zhang, 1999) within public databank files such as GeneBank, European Molecular Biology Laboratory, and DNA Data Bank of Japan. A computer software program, the Align Plus 5 (Sci Ed Software, Durham, N.C.) was used to compare sequence homology. This program is capable of revealing controversial bases which can be due to natural mutations in variant strains of the same species or due to sequencing errors. To ensure the reliability of sequence, only those regions with homologous molecules are used for our antisense design.

Identification of the target sites. The potential sites/regions within the DNA sequence that can be targeted for antisense design include the 5' cap region, the AUG translation initiation condon, the coding region downstream from AUG start condon, and the 3'-untranslated region for spliced (partial-length) sequence. In addition to the four potential sites mentioned above, the exon-intron junctions of the unspliced (full-length) sequence are also targeted (Phillips et al., 2000; Jansen and Zangemeister-Wittke, 2002; Phillips, 2001; Mohuczy and Phillips, 2002; Phillips and Zhang, 1999).

Selection of the length of antisense ODN. In designing antisense molecules, one has to consider two factors: one is the affinity of ODN to its target sequence, which is dependent upon the number of composition of complementary bases, and the availability of the target sequence, which is dependent upon the folding of the mRNA molecule (Lima et al., 1992; Sczakiel et al., 1993; Jaroszewski et al., 1993). The length of 15-20 bases is optimal because shorter sequences are more likely to be nonspecific while sequences longer than 25 are less able to enter cells and are also more likely to contain a repeat sequence of purines, which can false priming (Mohuczy and Phillips, 2002; Phillips and Zhang, 1999). Accordingly, the inventor limited the length to 15-20 base long in his pursuit of designing optimal antisense ODN molecules.

Evaluation of antisense ODN sequences. Once an antisense ODN sequence is configured, evaluation of its sequence to avoid potential pitfalls should be followed. The potential pitfalls in designing antisense ODN molecules include complicated secondary structures like loops and hairpins, the self-dimerization, the high GC content, the low stability, etc. (Mohuczy and Phillips, 2002; Phillips and Zhang, 1999). The secondary structures and self-dimerization make hybridization of ODN with its target mRNA more difficult. The high GC/AT ratio increases the nonspecific binding and the toxicity. The low stability decreases the resistant to degradation. Since the potential pitfalls for the design of antisense ODNs are applicable to the design of PCR primers, the Primer Designer 5, a software program developed by Sci Ed Software (Durham, N.C.) for PCR primer design, was used in our studies. The Primer Designer 5 can identify potential secondary structures and possible primer interactions (dimmers). The software program can analyze GC content, the melting temperature, and the stability. In addition, the Primer Designer 5 can check for false priming or other homologies between the primer (ODN) and the template (target mRNA). With the aid of this computer software program, the inventor was able to avoid potential pitfalls described above. Once an antisense ODN sequence is designed, a corresponding scrambled (the bases are identical while the entire sequence is random) as well as mismatch (two nucleotides different from antisense) ODNs are constructed for use as controls.

Screening of sequence specificity to exclude any significant overlapping with other mRNAs. One of the principal elements for antisense ODN to work successfully is that the hybridization is specific and unique for target mRNA, with no binding to other proteins. Thus, antisense ODN with any significant overlapping with sequence other than target gene should be excluded. To compare sequence homology between a given antisense ODN and all of the existing sequences listed in GenBank, European Molecular Biology Laboratgory, and DNA Data Bank of Japan, the inventor used BLAST search, a computer program available from NCBI web site.

Backbone modification. Modification of antisense ODN backbone improves the stability while reducing the danger of toxicity and nonspecific binding. One of the widely used modified ODN is phosphorothiate, where one of oxygen atoms in the phosphodiester bond between nucleotides is replaced with a sulfer atom (Phillips, 2001; Jaaskelainen and Urtti, 2002; Phillips and Zhang, 1999; Stein, 2001). In this study, the antisense and mismatch ODN molecules were synthesized by GenoMechanix, L.L.C. (Gainesville, Fla.) with phosphorothioate modifications in all bases.

Example 2

Preparations of Various Liposome and Polycation/Liposome Complexes and Determination of Their Transfection Efficiencies and Cytotoxicities Preparations of liposomes, polycation/liposome, and DNA/polycation/liposome complexes. Liposomes were prepared by a combination of reverse phase evaporation and sequential extrusion through polycarbonate membranes as described by Lee et al. (2003) and others (Szoka et al., 1980). The lipid mixtures of DOTAP/DOPE or DOTAP/CHO (a molar ratio of 1:1) were dissolved in chloroform and placed in a round-bottom flask filled with nitrogen gas. The organic solvent was removed by rotary evaporator (Micro Rotary Evaporator, Model 13275, equipped with a 3-ml pear shaped evaporating flask) (Ace Glass Inc., NJ). The thin lipid film was hydrated in 20 mM Hepes buffer (pH 7.4) to give a final concentration of 10 mg/ml cationic lipids. The lipid solution was sequentially extruded through polycarbonate membranes, ten times at pore size of 100 nm and seven times at 50 nm using high-pressure extrusion equipment (Thermobarrel Extruder, Model T.002) (Northern Lipids Inc., Vancouver, Canada) at room temperature. The cationic liposomes were filtered-sterilized through 0.22 µm-diameter filter. During the entire procedure, special care was exercised to avoid fatty acid oxidation. The methods described above for the preparation of liposomes are capable of yielding intermediate size (50-200 nm) and unilamella vesicles which are very homogeneous in size distribution (Szoka et al., 1980).

For preparations of polycation/liposome complexes (lipopolymers) and nucleic acid/polycation/liposome complexes (lipopolyplexes), pSV-β-gal (galactosidase) basic vector, pSV-β-gal reporter vector, antisense or mismatch/scrambled ODNs were mixed with polyethyleneimine (PEI) (linear 22 kDa or branched 25 kDa) of different weight ratios in 50 µl Hepes (20 mM, pH 7.4) buffer. Lipoplexes and lipopolyplexes were prepared by gently mixing 20 nmol of liposomes (the level of cationic lipids can be varied) in 50 µl of Hepes buffer with 1 µg of pSV-β-gal basic vector, pSV-β-gal reporter vector, antisense or mismatch ODNs in 50 µl of Hepes buffer with or without PEI. After incubation for 15 min at room temperature, the DNA/liposome complexes or the DNA/polycation/liposome complexes were added to the culture cells for transfection.

Measurements of transfection efficiencies and cytotoxicities of various liposome and polycation/liposome preparations. Six different lipopolymer complexes were prepared and their transfection efficiencies determined using human hepatoma cell line Huh7. The experiments include seven groups: 1) Lipofectin (DOTAM/DOPE, 1:1(w/w); DOTAM=N-[1-(2,3-dioleoyl)propyl]-N—N-trimethol ammonium chloride, DOPE=dioleyl-L-α-phosphatidylethanolamine, Gibco-BRL); 2) DOTAP/DOPE (DOTAP=1,2,-dioleoyl-3-[trimethylammonio]propane); 3) DOTAP/DOPE/PEI (22 kDa); 4) DOTAP/DOPE/PEI (25 kDa); 5) DOTAP/CHO (CHO=cholesterol); 6) DOTAP/CHO/PEI (22 kDa, PEI=polyehtyleneimine); and 7) DOTAP/CHO/PEI (25 kDa). Lipofectin, the most commonly used in vitro trasfection reagent, was included as a basis for comparison. It should be mentioned that the commercially available PEIs have two forms: linear ($\leq$22 kDa) and branched ($\geq$25 kDa). Both forms were included in our studies because both forms have been reported to be effective but with different efficiencies. Preliminary experiments have revealed that the optimal weight ratios were 1:1 for DOTAP/DOPE and DOTAP/CHO, and 1:1:0.06 for DOTAP/DOPE/PEI and DOTAP/CHO/PEI. Cultured human hepatoma (Huh 7) cells were transfected with pSV-β-gal expression plasmids complexed with various lipopolymer preparations as described in the preceding sections. The transfection efficiencies were determined by the expression of β-gal reporter gene using a commercially available kid at 48 h after transfection. The cytotoxic effects are quantified based on the leakage of lactate dehydrogenase (LDH) from the cells.

Example 3

Assays of the In Vitro Efficacies of Antisense ODN Candidates Using Cultured Human Cell Lines The "gold-standard" of antisense efficacy is down regulation of its molecular target, most often protein expression with or without down regulation of mRNA expression (Stein, 2001). In these studies, the in vitro efficacies of antisense ODN candidates to inhibit the transcription and translation of $PLA_2$ genes were determined as described by Lee et al. (2003) with modification.

In Vitro Efficacies on the Inhibition of $sPLA_2$ Protein Expression. For $sPLA_2$ efficacy assay, human hepatocellular carcinoma cell line HepG2 (obtained from ATCC, Manassas, Va.) was used. HepG2 cells were maintained in culture medium (DMEM supplemented with 10% fetal bovine serum, 100 international units/ml of penicillin, and 100 µg/ml of streptomycin) at 37° C. under 5% $CO_2$. Cells ($3 \times 10^5$) were seeded in 2 ml of medium in 6-well culture plates for 18-24 h until the cell density reaches 50% confluency. The culture medium was replaced with 0.9 ml of OPTI-MEM I medium prior to adding 0.1 ml of DNA/polycation/liposome (DNA/DOTAP/DOPE/PEI) complexes. After incubation for 4 h at 37° C. under 5% $CO_2$, 1 ml of culture medium was added and incubated for another 40 h. At time of harvest, cells were washed with PBS and then lysed with 200 µl of buffer containing 150 mM NaCl, 20 mM Tris-HCl (pH 7.4), 1% Triton X-100, 1% Na-deoxycholate, 1 mM EDTA, 0.1% SDS, 1 mM PMSF, 0.6 µg aprotinin, and 0.6 µg leupeptin. The mixtures were centrifuged and the resultant supernants (lysates) were used for Western blot analysis. For Western blot analysis, 30 µl of lysate was subjected to SDS-PAGE (15% polyacrylamide gel). Proteins separated by SDS-PAGE were transferred to a polyvinylidene fluoride membrane. Non-specific binding sites were blocked with 5% (wt/vol) of nonfat dry milk in a buffer containing 20 mM Tris-HCl (pH 7.6), 150 mM NaCl, and 0.1% Tween-20 for 1.5 h at room temperature. The membranes were incubated with specific antibodies against $sPLA_2$ IIa (Cat # ab23705 from Abcam, Cambridge, Mass.) and β-actin (Sigma, St. Louis, Mo.) for 2.5 and 1 h, respectively, at room temperature, followed by the use of anti-rabbit IgG, horseradish peroxidase-labeled secondary antibodies (GE Healthcare, UK). Blots were developed using a chemiluminescent detction system and exposed to Hyperfilm-ECL (GE Healthcare, UK). Protein bands on the film were scanned with a Hewlett-Packard scanner (Scan Jet 5370C) and the relative densities were quantified by a Jandel Scientific Software program (Sigma Gel).

In Vitro Efficacies on the Inhibiton of $cPLA_2$ Protein Expression. For $cPLA_2$ efficacy assay, human monocytic leukemia cell line U937 (obtained from ATCC, Manassas, Va.) was used. The procedures for cell culture, oligonucleotide transfection and Western blot analysis were similar to those for $sPLA_2$ efficacy assay except: 1) DMEM was replaced with RPMI 1640 in culture medium; 2) polyacrylamide gel concentration was reduced to 10%, and 3) a monoclonal antibody raised specifically against cPLA$_2$ IVa (Cat #SC-454 from Santa Cruz Biotechnology) was used as a primary antibody.

Example 4

Determinations of Clinical Efficacies of Antisense Oligonucleotides in Intact Animals Using Survival Rates as Efficacy Endpoints Those antisense ODNs that share sequence homology with human and rat species (human/rat overlap sequences) and proven to be efficacious in vitro were employed in this study. With these overlap sequences, knowledge gained from rat experiments can provide a basis for future human trials. Clinically, treatment of sepsis has proven to be highly ineffective in preventing the eventual outcome, i.e., the mortality (Steinhauser et al., 1999). Thus, the survival rates (mortality rates) were used as endpoints for our clinical efficacy determination. Male Sprague-Dawley rats (Harlan Laboratories) weighing from 180-190 g were used as experimental animals.

Insertion of a femoral vein catheter to serve as an access port for daily intravenous injections of oligonucleotides and saline. Insertion of a femoral vein catheter into inferior vena cava was performed based on a procedure described by Yang et at (2005). Under isoflurane anesthesia (3-5% delivered via a precision vaporizer, 2.0 L/m O$_2$ flow), a 2-cm ventral skin incision was made along the crease formed by the abdomen and right thigh. Blunt dissection of the adductor muscle was used to visualize the right femoral vein. Five to ten millimeters of vessel was mobilized and a sterile catheter (2F silastic tubing) was inserted into the femoral vein and advanced to the inferior vena cava until its tip reached at the approximate level of the xiphisternum. The catheter was fixed with two 5-0 silk ligature, tunneled subcutaneously to the dorsum of the neck and drawn back up through the skin. A 1-cm distal end of tubing serving as an access port for oligo and saline administration was sealed with a stainless steel plug. The femoral vein catheter was flushed through the access port using sterile 0.8 ml of 4 U/ml heparin/saline solution, followed by injection of 0.05 ml of 50 U/ml heparin/saline lock solution. Prior to the recovery, 0.5% bupivacaine was infused s.c. at the edges of the skin incision. Buprenorphine HCL, 0.5 mg/kg s.c., was administered for added postoperative pain control three times at 12-h intervals. Signs of local skin inflammation, if present, were treated with topical application of Triple Antibiotic Ointment. Catheter potency was maintained by periodic flushing with sterile heparinized saline (4 U/ml).

Rat sepsis model. Three days after the femoral vein catheterization, sepsis was induced by cecal ligation and puncture (CLP) as described by Wichterman et al. (1980) with minor modification. Under isoflurane anesthesia (3-5% delivered via a precision vaporizer, 2.0 L/m O$_2$ flow), a laparotomy was performed and the distal cecum was externalized and ligated with a 3-0 silk ligation and the wall punctured twice with an 18-gauge needle. The cecum was then returned to the peritoneal cavity and the abdomen was closed in two layers. The muscle layer was closed using an absorbable suture material (Vicryl, PDS) and the skin was opposed using a non-absorbable suture material (silk). Buprenorphine HCl, 0.5 mlg/kg s.c., was administered for added postoperative pain control three times at 12-h intervals. All animals were supplemented with subcutaneous 4 ml/100 g body weight of normal saline at the time of surgery. Animals were observed constantly during the recovery period. Once fully recovered, animals were returned to their holding room and observed every two hours until they reached their endpoints. The septic rat model induced as described above exhibited a typical biphasic change: an initial hypermetabolic/hyperglycemic phase (4.5-9 h post-CLP) (characterized by elevated HR, CO, LV+dP/dtmax, body temperature, blood glucose, blood lactate, and circulating catecholamines with normal MABP, LVEDP, and LV−dP/dtmax) followed by a hypometabolic/hypoglycemic phase (13.5-18 h post-CLP) (characterized by decreased body temperature, HR, CO, MABP, LV±dP/dtmax, and blood glucose with elevated LVEDP, blood lactate, and circulating catecholamines) (Tang and Liu, 1996). These features were of typical septic shock syndrome, which mimics closely the clinical state of sepsis.

Protocols for the administration of antisense ODNs using a CLP-induced septic rat model. Experiments consisted of 4 groups: 1) CLP+saline (PBS); 2) CLP+antibiotic; 3) CLP+antibiotic+mismatch ODN; and 4) CLP+antibiotic+antisense ODN. Numbers of animals were 16 in Gp 1, 25 in Gp 2, 16 in Gp 3, and 17 in Gp 4. All animals have femoral vein catheters placed approximately 3 days prior to CLP procedure. Immediately following CLP procedure, Gp 2-4 animals received a concurrent administration of antibiotic (Baytril, obtained from Bayer Healthcare, KS) and oligonucleotides. Antibiotics were given subcutaneously, once daily at 12 mg/kg (1.2 ml/100 g), for up to 20 days. It is noteworthy that antibiotics have been shown to improve the time and rate of survival and are clinically relevant as septic patients are on antibiotics as first line therapy. Oligonucleotides (antisense or mismatch ODNs) were administered intravenously via femoral vein catheter, once daily at the following doses (<0.4 ml/100 g): 2 mg/kg for days 1-6; 1.8 mg/kg for days 7-10; 1.6 mg/kg for days 11-14; and 0.8 mg/kg for days 15-20. All animals were followed up to 35 days and the mortality rates were used as experimental endpoints. The sequences of antisense ODNs used were 5'-TTGGGGGATCCTCTGCCACC-3' for sPLA$_2$ (SEQ ID NO: 13) (S23) and 5'-AAAGGCACTGCCCCAGA-CAC-3' (SEQ ID NO:18) (S56) for cPLA$_2$. The 2-base altered sequences were used as their corresponding mismatch ODNs: 5'-TTGGTGGATCCTCTGGCACC-3' for sPLA$_2$ (SEQ ID NO:22) and 5'-AAAGTCACTGCCCCACACAC-3' for cPLA$_2$ (SEQ ID NO:23). It is noteworthy that unlike in vitro cell culture systems, a delivery system does not appear to be necessary for an antisense oligo to function effectively when it is administered to an intact animal (Dias and Stein, 2002; Moschos et al. 2008). Thus, naked phosphorothioate oligonucleotides were used in the in vivo animal studies.

All oligonucleotides used in this study were synthesized by GenoMechanix, LLC (Gainesville, Fla.) using the standard solid phase phosphoramidite chemistry in an automated Expedite DNA Synthesizer. The synthesis was monitored using the release of the Trityl moiety from the Dimethoxytrityl group on the 2-cyanoethyl phosphoramidite. Each phosphodiester backbone was modified during the synthesis using the standard Beaucage reagent. Following the completion of synthesis, the ODNs were deprotected and released from the controlled pore glass matrix using ammonium hydroxide at 55 C for 16-18 hrs. The released ODN was subjected to gel filtration using a Sephadex G-25 column to remove ammonium hydroxide and low molecular weight impurities generated during the synthesis. The crude ODN preparation was subjected to an ion exchange chromatography on a QAE-Sephadex resin and bound full length ODN was eluted using a salt (NaCl) gradient in 10 mM phosphate buffer at pH 6.8. The eluted material was concentrated and subjected to hydrophobic HPLC on a C18 column. Purified ODN was eluted using an acetonitrile gradient (5% to 50%) in 0.05M Triethylamine buffer at pH 6.0. The purified ODN eluted from the column was lyophilized and then subjected to a final gel filtration on a Sephadex G-25 column equilibrated in sterile water. The eluted ODN was lyophilized followed by resuspension in 70% ethyl alcohol (HPLC grade) and re-lyophilized. The purity of ODNs was tested by hydrophobic HPLC on a C18 resin using an acetonitrile gradient (0%-35%) in 0.01M Triethylamine buffer at pH 6.0%. All ODNs were >95% pure. Two antisense oligos (SEQ ID NOS: 13 and 18) or two mismatch oligos were dissolved in saline (PBS) to give a final concentration of 1 mg/ml for each oligo. The mixtures were used either freshly or stored at 4° C. and used within 3 days. According to the manufacturer, mixing of two antisense oligos or two mismatch oligos in one preparation (PBS) did not form seconday structures or oligo parings, indicating that their original structures remained intact.

Statistical analysis. The 35-day mortality was used as primary efficacy endpoint. The survival curves were analyzed by Cox proportional-hazards regression model. A p value of less than 0.05 was accepted as statistically significant.

Example 5

Putative Antisense ODN Candidates

Using the procedures described above, the inventor designed a list of antisense ODN molecules that met all the criteria required for an antisense ODN to function effectively and specifically for its target gene. The results are shown in FIGS. 1-6 and Table 1. FIG. 1 depicts the base pair positions of antisense ODN candidates designed specifically against human unspliced sPLA$_2$ IIa DNA sequence, M22431.1 while FIG. 2 depicts those against human spliced sPLA$_2$ IIa mRNA sequence, NM_000300.3. FIG. 3 shows the base pair positions of antisense ODN candidates designed specifically against human unspliced cPLA$_2$ IVa DNA sequence, AY552098.1 while FIG. 4 shows those against human spliced cPLA$_2$ IVa mRNA sequence, NM_024420.2. FIG. 5 depicts the base pair positions of antisense ODN candidates designed specifically against human/rat overlap sPLA$_2$ IIa mRNA sequences, NM_000300.3 (human) and M25148.1 (rat) while FIG. 6 shows those against human/rat overlap cPLA$_2$ IVa mRNA sequences, NM_024420.2 (human) and BC070940.1 (rat). There were a total of 105 sequences that have met the design criteria as putative antisense ODN candidates against both sPLA$_2$ and cPLA$_2$ genes in human species from which 36 sequences have shared common sequence homology with rat species (human/rat overlap sequences) (Table 1).

TABLE 1

Summary of putative antisense ODN candidates targeting sPLA2 and cPLA2 genes, that have met the design criteria

| Number of antisense ODNs that have met the design criteria | Target | Species | Detail |
| --- | --- | --- | --- |
| 15 | sPLA2 IIa, unspliced | human | FIG. 1 |
| 11 | sPLA2 IIa, spliced | human | FIG. 2 |
| 22 | cPLA2 IVa, unspliced | human | FIG. 3 |
| 21 | cPLA2 IVa, spliced | human | FIG. 4 |
| 6 | sPLA2 IIa, spliced | human/rat (overlap) | FIG. 5 |
| 30 | cPLA2 IVa, spliced | human/rat (overlap) | FIG. 6 |

Example 6

An Optimal Delivery System for Antisense ODNS in In Vitro Efficacy Experiments

Six different lipopolymer complexes were prepared as described above. The vesicle size distribution of various liposome preparations was analyzed by Northern Lipids, Inc. (Vancouver, Canada) and their transfection efficiencies were determined using human hepatoma cell line Huh7. FIG. 7 depicts the vesicle size distribution of a polycation/liposome complex, DOTAP/DOPE/PEI (25 kD), prepared in this laboratory. This liposome preparation had a mean vesical diameter of approximately 83 nm and was very homogeneous in size distribution. FIG. 8 shows the transfection efficiencies of six different liposome preparations. The transfection efficiencies for DOTAP/DOPE and DOTAP/CHO liposomes were approximately 15-fold higher than that for Lipofection (DOTMA/DOPE). When these liposome preparations were complexed with PEIs, their transfection efficiencies were increased to 30-40-fold higher than that of Lipofectin. The cytotoxicities for various lipopolymers, except for DOTAP/CHO/PEI complexes, were minimal, i.e., less than 5% cell lysis, as judged by leakage of LDH (FIG. 8). These data demonstrate that DOTAP/DOPE/PEI (25 kD) has a highest transfection efficiency with a low cellular toxicity, among various preparations tested. Accordingly, this PEI-based cationic lipopolymer preparation was used as a nonviral delivery system for in vitro efficacy studies.

Example 7

Effective Antisense Molecules Targeting SPLA$_2$ and CPLA$_2$ Genes

The in vitro efficacies of putative antisense ODN candidates that met the design criteria (FIGS. 1-6) were tested using a nonviral delivery system (FIG. 8) and human cultured cell lines. FIG. 9 depicts the effect of SEQ ID NOS: 1 (S101) and 2 (S104) on the inhibition of sPLA$_2$ protein expression in human hepatoma HepG2 cell line. The sPLA$_2$ IIa protein expression was inhibited by 53-68% by SEQ ID NO:1, and by 67-72% by SEQ ID NO:2, at concentrations between 5-10 μM. As shown in FIG. 10, the cPLA$_2$ IVa protein expression was inhibited dose-dependly by 25-56% at concentrations from 5 to 15 μM in human leukemia U937 cells transfected with SEQ ID NO:9 (S707). FIGS. 11 and 12 show the in vitro inhibition of target gene protein expression by antisense ODNs that shared common sequence homology between human and rat species (Human/rat overlap sequences), SEQ ID NOS:13 (S23) and 18 (S56), in human cultured cell lines. The sPLA$_2$ IIa protein expression was reduced dose-dependly by 51-81% at concentrations between 5-15 μM in human Hepatoma HepG2 cells transfected with SEQ ID NO:13 (S23) (FIG. 11). Similarly, the cPLA$_2$ IVa gene transcript was down-regulated by 67-73% at concentrations between 5-15 μM in human leukemia U937 cell transfected with SEQ ID NO:18 (S56) (FIG. 12). Table 2 summarizes the composition, the sequence, and the extent of inhibition on target gene expression, of antisense molecules that proven to be efficacious in down-regulating sPLA$_2$ and cPLA$_2$ genes in cultured cell systems. The results demonstrate that 21 of the 105 (20%) antisense ODN candidates that met the design criteria are efficacious in inhibiting the expression of their respective target proteins.

TABLE 2

The composition, the sequence, and the extent of inhibition on target protein expression, of antisense molecules that proven to be efficacious in in vitro cell culture systems

| SEQ ID NO | Name | Base composition and sequence | Target | % Inhib. target protein expression (5-20 µM) |
|---|---|---|---|---|
| 1 | S101 | 5'-GTCTTCATGGTAAGAGTT-3' | human sPLA2 | 53-68 |
| 2 | S104 | 5'-TCTTACCAAAGATCATGAT-3' | | 67-72 |
| 3 | S109 | 5'-GGACTCTTACCACAG-3' | | 20-28 |
| 4 | S113 | 5'-CTCACCGATCCGTTGCAT-3' | | 27-41 |
| 5 | S114 | 5'-CCTCACCGATCCGTTGCAT-3' | | 26-42 |
| 6 | S311 | 5'-TTTATTCAGAAGAGA-3' | | 60-75 |
| 7 | S705 | 5'-GCTCCACCTGGAAAT-3' | human cPLA2 | 29-36 |
| 8 | S706 | 5'-GTGCTCCACCTGGAAA-3' | | 16-31 |
| 9 | S707 | 5'-GAATACTGGTGCTCCAC-3' | | 25-56 |
| 10 | S722 | 5'-TTTATCACCTGCAAATAG-3' | | 21-46 |
| 11 | S503 | 5'-CCTCAATGCCTCTAGCTTTC-3' | | 29-38 |
| 12 | S508 | 5'-TCTATAAATGACATTTTGG-3' | | 30-43 |
| 13 | S23 | 5'-TTGGGGGATCCTCTGCCACC-3' | human/rat sPLA2 (overlap) | 51-81 |
| 14 | S24 | 5'-CATCCTTGGGGGATC-3' | | 57-83 |
| 15 | S25 | 5'-GTGCCACATCCACGT-3' | | 56-62 |
| 16 | S26 | 5'-GTGCCACATCCACGTTTCTC-3' | | 43-60 |
| 17 | S45 | 5'-AGAATCCCACCATGGC-3' | human/rat cPLA2 (overlap) | 24-62 |
| 18 | S56 | 5'-AAAGGCACTGCCCCAGACAC-3' | | 67-73 |
| 19 | S58 | 5'-TTCCCAGCACGTCCTTCTC-3' | | 47-73 |
| 20 | S60 | 5'-GGGATACGGCAGGTT-3' | | 64-69 |
| 21 | S63 | 5'-AGGATCAATCTTTGG-3' | | 54-60 |

Example 8

Clinical Efficacies of Antisense ODNS in Intact Septic Animals Using Mortality as Primary Efficacy Endpoint Clinical efficacies of antisense ODNs in intact septic animals were determined as described above. Male Sprague-Dawley rats were used as experimental animals. Sepsis was induced by cecal ligating and puncture (CLP) technique. Immediately after CLP procedure, antibiotic was given s.c. followed by i.v. injection of antisense/mismatch oligonucleotides. Antibiotics and oligonucleotides were administered once daily for 20 days. Animals were followed up to 35 days using mortality as primary efficacy endpoint. For antibiotic treatment, Baytril was selected because it is a broad spectrum antibiotic that has been proven clinically effective in treating animals with a wide variety of bacterial infections, including many caused by gram-negative or gram-positive aerobes and anaerobes. For antisense ODN treatment, two antisense oligos, one against sPLA$_2$ (SEQ ID NO: 13) and the other against cPLA$_2$ (SEQ ID NO:18) were combined. The two-base mismatch oligos were used as their corresponding controls.

FIG. 13 depicts clinical efficacies of antisense ODNs in intact septic animals using mortality as primary efficacy endpoint. Without any treatment, sepsis had a median survival time of 2 days and a zero (0) % survival rate at day 14 (Gp 1). With antibiotic treatment, the septic animals had a median survival time of 6 days and a 35-day (efficacy endpoint) survival rate of 28.0% (Gp 2). With concurrent treatment of antibiotics and antisense ODNs, the median survival time was increased from 6 to 35 days and the 35-day survival rate was increased from 28.0 to 58.8% (Gp 4; Gp 4 vs Gp 2). Analyses of survival curves using Cox proportional-hazards regression model indicate that the beneficial effects of antibiotics (Gp 1 vs Gp 2) and the additional beneficial effects of antisense oligonucleotides (Gp 4 vs Gp 2) were statistically significant ($p$ <0.05). These results demonstrate that the use of two different antisense oligonucleotides, one targeted sPLA$_2$ while the other aimed at cPLA$_2$ genes, significantly improved the time, as well as the rates of survival of septic animals. It is of interest to note that with concurrent treatment of antibiotics and mismatch oligonucleotides, the median survival time and the 35-day survival rate remained unaffected as compared to antibiotics alone. (Gp 3 vs Gp 2; $p$>0.05). Putting these results together, it is apparent that the beneficial effects of antisense oligonucleotides in septic animals is specifically derived from antisense molecules.

In summary, these data clearly demonstrate that the use of two different oligonucleotides, one targeted sPLA$_2$ and the other aimed at cPLA$_2$ genes, in conjunction with antibiotics, greatly improve the eventual outcome", i.e., an absolute reduction in 35-day mortality of 30.8%, in animals with sepsis. Since the antisense ODNs used in this study share common sequence homology in human and rat species, the rat study can thus provide a basis for subsequent human clinical trials.

Example 9

Effects of Antisense ODN Treatment on the SPLA2 HA and CPLA2 IVA Protein Expression in Various Organs of Septic Animals FIG. 14 shows the effects of antisense ODN treatment on the sPLA$_2$ IIa and cPLA$_2$ IVa protein expression, as determined by Western blot analyses, in various organs harvested from postmortem septic rats. It is noteworthy that among the three major organs examined, sPLA$_2$ IIa was found to be abundantly distributed in liver and kidney (liver= kidney>>heart) while cPLA$_2$ IVa was preferentially expressed in heart (heart>>kidney=liver). Septic animals treated with antisense ODNs for 6 days, the sPLA$_2$ IIa and cPLA$_2$ IVa protein expression was reduced by 58% and 18%, respectively, in liver while no change was found in heart and kidney. Septic animals treated with antisense ODNs for 17-20 days, the sPLA$_2$ IIa and cPLA$_2$ IVa protein expression was down-regulated in all three major organs: the inhibition for sPLA$_2$ IIa was 54%, 45% and 43%, respectively, in liver, heart, and kidney; the inhibition for cPLA$_2$ IVa was 45%, 51% and 61%, respectively, in liver, heart, and kidney. These findings clearly demonstrate that the inhibition on sPLA$_2$ IIa and cPLA$_2$ IVa protein expression was achieved in vivo in major organ systems with antisense oligo treatment. These data together with the survival data presented in FIG. 13 provide a mechanistic link between the inhibition of target protein expression in major organs and the beneficial effect of antisense ODNs on the improvement of the eventual clinical outcome.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. An antisense oligonucleotide of 15 to 25 bases comprising a sequence selected from the group consisting of SEQ ID NO: 13 (5'-TTGGGGGATCCTCTGCCACC-3') or SEQ ID NO: 18 (5'-AAAGGCACTGCCCCAGACAC-3').

2. The antisense oligonucleotide of claim 1, dispersed in a pharmaceutical buffer, diluent or excipient.

3. The antisense oligonucleotide of claim 1, formulated in a lipid carrier.

4. The antisense oligonucleotide of claim 1, further comprising a nuclear targeting sequence.

5. The antisense oligonucleotide of claim 1, comprising one or more modified or non-natural nucleotides.

6. An antisense oligonucleotide of 18 to 25 bases comprising a sequence selected from the group consisting of SEQ ID NO: 13 (5'-TTGGGGGATCCTCTGCCACC-3') or SEQ ID NO: 18 (5'-AAAGGCACTGCCCCAGACAC-3').

7. An antisense oligonucleotide of 18 to 25 bases comprising a sequence selected from the group consisting of -, SEQ ID NO:13 (5'-TTGGGGGATCCTCTGCCACC-3'), or SEQ ID NO:18 (5'-AAAGGCACTGCCCCAGACAC-3') and the selected oligonucleotide when administered to a predictive animal model that mimics a disease pathogenesis process in humans causes a reduction of the protein product encoded by the target gene by at least 20% in a major organ selected from the group comprising liver, kidney, or heart.

8. The antisense oligonucleotide 1, wherein said antisense oligonucleotide is 15-20 bases.

9. The antisense oligonucleotide of claim 1, wherein said antisense oligonucleotide consists of a sequence selected from the group consisting of SEQ ID NO: 13 (5'-TTGGGG-GATCCTCTGCCACC-3') or SEQ ID NO: 18 (5'-AAAG-GCACTGCCCCAGACAC-3').

10. A method of reducing phospholipase $A_2$ expression in a cell comprising contacting said cell with two antisense oligonucleotides of 15 to 25 bases and comprising the sequences of SEQ ID NO: 13 (5'-TTGGGGGATCCTCTGC-CACC-3') or SEQ ID NO: 18 (5'-AAAGGCACTGCCCCA-GACAC-3').

11. The method of claim 10, wherein said cell is located in a living subject and said antisense oligonucleotide is dispersed in a pharmaceutically acceptable buffer, diluent or excipient.

12. The method of claim 11, wherein said subject suffers from sepsis, septic shock, inflammation, inflammatory bowel disease, trauma, rheumatoid arthritis, adult respiratory distress syndrome (ARDS), asthma, rhinitis, diabetes type II, psoriasis, ischemic disease, atherosclerosis, restenosis, platelet aggregation, ulceration or cancer.

13. The method claim 11, wherein said antisense oligonucleotide is formulated in a lipid carrier.

14. The method of claim 10, further comprising a nuclear targeting sequence.

15. The method of claim 10, comprising one or more modified or non-natural nucleotides.

16. The method of claim 10, wherein said antisense oligonucleotide is 15-25 bases or 15-20 bases.

17. The method of claim 10, wherein two antisense oligonucleotide consists of an antisense oligonucleotide of 18 to 25 bases: one comprising SEQ ID NO:13 (5'-TTGGGGGATC-CTCTGCCACC-3') and the other comprising SEQ ID NO:18 (5'-AAAGGCACTGCCCCAGACAC-3'), and when administered to a predictive animal model that mimics a disease pathogenesis process in humans the selected antisense oligonucleotides cause a reduction of both protein products encoded by the genes targeted by said oligonucleotides by at least 20% in a major organ selected from the group comprising liver, kidney, or heart.

* * * * *